(12) United States Patent
Lee

(10) Patent No.: US 10,484,777 B2
(45) Date of Patent: Nov. 19, 2019

(54) EAR WEARABLE DEVICE

(71) Applicant: Samsung Electronics Co., Ltd., Gyeonggi-do (KR)

(72) Inventor: Ki-Eon Lee, Seoul (KR)

(73) Assignee: Samsung Electronics Co., Ltd., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 16/023,096

(22) Filed: Jun. 29, 2018

(65) Prior Publication Data

US 2019/0014403 A1  Jan. 10, 2019

(30) Foreign Application Priority Data

Jul. 4, 2017 (KR) ........................ 10-2017-0084762

(51) Int. Cl.
*H04R 1/00* (2006.01)
*A61B 5/024* (2006.01)
*A61B 5/00* (2006.01)
*H04R 1/10* (2006.01)

(52) U.S. Cl.
CPC ....... *H04R 1/1041* (2013.01); *A61B 5/02416* (2013.01); *A61B 5/02438* (2013.01); *A61B 5/6817* (2013.01); *H04R 1/105* (2013.01); *H04R 1/1016* (2013.01); *H04R 1/1025* (2013.01); *H04R 1/1058* (2013.01); *H04R 1/1066* (2013.01); *H04R 2420/07* (2013.01)

(58) Field of Classification Search
None
See application file for complete search history.

(56) References Cited

U.S. PATENT DOCUMENTS

2004/0203506 A1* 10/2004 Gantz ................. H04M 1/05
455/90.3
2005/0064918 A1*  3/2005 Medhin ................ H04M 1/05
455/575.2
2006/0215864 A1   9/2006 Espersen et al.
(Continued)

FOREIGN PATENT DOCUMENTS

EP         1 429 580 A1    6/2004
JP       2002-112377 A    4/2002
(Continued)

OTHER PUBLICATIONS

Satoru et al. "Earphone." English copy via Google translate of WO2014061646. 10 pages. Apr. 24, 2014.*
European Search Report dated Oct. 31, 2018.

*Primary Examiner* — Qin Zhu
(74) *Attorney, Agent, or Firm* — Cha & Reiter, LLC.

(57) ABSTRACT

An ear wearable device comprising: a housing comprising a portion shaped to be inserted into a concha of the ear, a speaker disposed inside the housing and configured to be disposed in an auditory canal when the housing is inserted into the concha of the ear, a button emerging from a hole formed in the housing, an elastic member disposed in the housing and elastically resisting an external force against the button; and a movable member including a portion protruding through an opening formed in the housing, and configured to be pushed into the opening or pulled away from the opening such that the protruding portion can be pushed or pulled when the button is pressed.

20 Claims, 16 Drawing Sheets

(56) References Cited

U.S. PATENT DOCUMENTS

| | | | |
|---|---|---|---|
| 2006/0215868 A1* | 9/2006 | Okamura | H04R 1/105 381/381 |
| 2008/0298625 A1* | 12/2008 | Prince | H04R 1/105 381/381 |
| 2008/0310666 A1* | 12/2008 | Wengreen | H04R 1/026 381/381 |
| 2009/0052716 A1* | 2/2009 | Yamaguchi | H04R 1/1058 381/378 |
| 2009/0110227 A1* | 4/2009 | Prince | H04R 1/105 381/380 |
| 2012/0237068 A1* | 9/2012 | Fretz | H04R 25/656 381/330 |
| 2015/0071477 A1* | 3/2015 | Mainini | H04R 1/105 381/380 |
| 2015/0110320 A1* | 4/2015 | Liu | H04R 1/1016 381/322 |
| 2016/0249133 A1* | 8/2016 | Sorensen | H04R 1/1041 |
| 2017/0041720 A1 | 2/2017 | Oxford | |
| 2017/0048614 A1 | 2/2017 | Gobeli et al. | |
| 2017/0048616 A1 | 2/2017 | Kraft et al. | |
| 2017/0055060 A1 | 2/2017 | Chan | |
| 2017/0064434 A1 | 3/2017 | Campbell et al. | |
| 2017/0245040 A1* | 8/2017 | Hankey | H04M 1/05 |
| 2018/0295439 A1* | 10/2018 | Garrett | H04R 1/1016 |

FOREIGN PATENT DOCUMENTS

| | | | |
|---|---|---|---|
| WO | 02/54825 A2 | 7/2002 | |
| WO | WO-2006107274 A1 * | 10/2006 | H04M 1/05 |
| WO | 2011/077160 A1 | 6/2011 | |
| WO | 2014/051416 A1 | 4/2014 | |
| WO | 2017/019885 A1 | 2/2017 | |

* cited by examiner

EAR WEARABLE DEVICE

CROSS-REFERENCE TO RELATED APPLICATION(S)

This application is based on and claims priority under 35 U.S.C. § 119 to Korean Patent Application No. 10-2017-0084762, filed on Jul. 4, 2017, in the Korean Intellectual Property Office, the disclosure of which is incorporated by reference herein in its entirety.

BACKGROUND

1) Field Various embodiments of the present disclosure relate to a size-adjustable ear wearable device.

2) Description of Related Art

The above information is presented as background information only to assist with an understanding of the present disclosure. No determination has been made, and no assertion is made, as to whether any of the above might be applicable as prior art with regard to the present disclosure.

Electronic devices are being provided in various forms such as a smart phone, a tablet Personal Computer (PC), and a Personal Digital Assistant (PDA), according to the development of digital technologies. Electronic devices are also being developed in a user wearable form in order to improve portability and a user's accessibility.

An electronic device may be an ear wearable device that can be worn on the user's ear. The ear wearable device may be connected to an external electronic device, and the external electronic device may transmit audio contents to the ear wearable device. The ear wearable device may output the audio contents received from the external electronic device through a speaker.

SUMMARY

An ear wearable device may take a form of being worn in the helix of the ear. Since the shape of the auricle varies from person to person, for an ear wearable device, a plurality of portions (e.g., wing tips) to be coupled to the helix of the ear may be configured to be detachable and may be provided in various sizes. When the above-mentioned portion of the ear wearable device (hereinafter, referred to as a "detachable member") is selectively used according to the shape of the auricle, the ear wearable device may have a size that can be coupled to the auricle without shaking. However, when selecting a detachable member suitable for the shape of the auricle, it is troublesome to attach and detach a plurality of detachable members one by one to the ear wearable device. In addition, the size of the ear wearable device is changeable only when carrying the detachable members. In addition, since detachable members of some sizes are provided, there is a limitation in selection for a precise detachable member.

Various embodiments of the present disclosure may provide an ear wearable device, which is configured such that a portion to be coupled to the helix of the ear can be easily resized without replacing the portion.

Various embodiments of the present disclosure may provide an ear wearable device, which enables a portion to be coupled to the helix of the ear to be precisely resized in comparison with a type of replacing the portion to be coupled to the groove of an auricle.

According to an embodiment of the present disclosure, an ear wearable device comprises a housing comprising a portion shaped to be inserted into a concha of the ear, a speaker disposed inside the housing and configured to be disposed in an auditory canal when the housing is inserted into the concha of the ear, a button emerging from a hole formed in the housing, an elastic member disposed in the housing and elastically resisting an external force against the button, and a movable member including a portion protruding through an opening formed in the housing, and configured to be pushed into the opening or pulled away from the opening such that the protruding portion can be pushed or pulled when the button is pressed.

An ear wearable device according to an embodiment of the present disclosure may be configured such that the size of the ear wearable device can be adjusted easily and precisely in the manner of pushing or pulling a portion used for placement into the helix of the ear into or out of the housing in a state in which a button disposed in the housing is pushed, without replacing a portion coupled to the helix of the ear. In addition, since the portion coupled to the helix of the ear does not have to be provided as replaceable detachable members of various sizes, not only the cost can be reduced but also the convenience of not having the detachable members separately can be provided.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
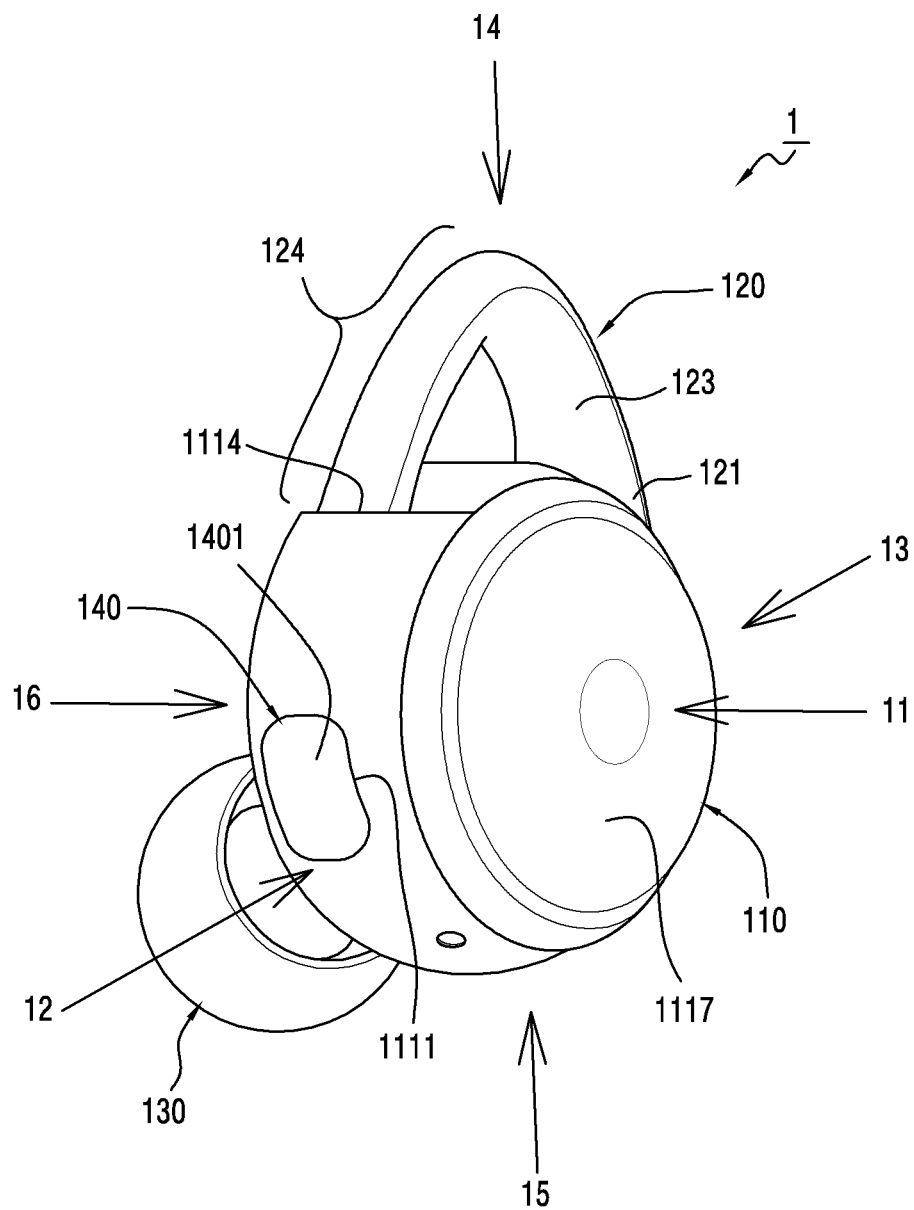
FIG. 1 is a perspective view of an ear wearable device according to an embodiment.

Hereinafter, various embodiments of the present disclosure will be described with reference to the accompanying drawings. The embodiments and the terms used therein are not intended to limit the technology disclosed herein to specific forms, and should be understood to include various modifications, equivalents, and/or alternatives to the corresponding embodiments. In describing the drawings, similar reference numerals may be used to designate similar constituent elements. A singular expression may include a plural expression unless they are definitely different in a context. As used herein, singular forms may include plural forms as well unless the context clearly indicates otherwise. The expression "a first", "a second", "the first", or "the second" may modify corresponding elements regardless of the order or importance, and is used only to distinguish one element from another element, but does not limit the corresponding elements. When an element (e.g., first element) is referred to as being "(functionally or communicatively) connected," or "directly coupled" to another element (second element), the element may be connected directly to the another element or connected to the another element through yet another element (e.g., third element).

The expression "configured to" as used in various embodiments of the present disclosure may be interchangeably used with, for example, "suitable for", "having the capacity to", "designed to", "adapted to", "made to", or "capable of" in terms of hardware or software, according to circumstances. Alternatively, in some situations, the expression "device configured to" may mean that the device, together with other devices or components, "is able to".

FIG. 1 is a perspective view of an ear wearable device according to an embodiment. FIGS. 2A, 2B, 2C, 2D, 2E and 2F are views illustrating appearances of the ear wearable device according to an embodiment viewed from various directions; FIG. 2A is a front view of an ear wearable device 1 viewed in a first direction 11 in FIG. 1. FIG. 2B is a left view of the ear wearable device 1 viewed in a second direction 12 in FIG. 1. FIG. 2C is a right view of the ear wearable device 1 viewed in a third direction 13 in FIG. 1. FIG. 2D is a top view of the ear wearable device 1 viewed in a fourth direction 14 in FIG. 1. FIG. 2E is a bottom view of the ear wearable device 1 viewed in a fifth direction 15 in FIG. 1. FIG. 2F is a back view of the ear wearable device 1 viewed in a sixth direction 16 in FIG. 1.

Referring to FIGS. 1, 2A, 2B, 2C, 2D, 2E and 2F, the ear wearable device 1 may include a housing 110 and a movable member 120 coupled to the housing 110 to be movable inward or outward of the housing 110. According to an embodiment, at least a portion of the movable member 120 protruding out of the housing 110 may be used for coupling the ear wearable device 1 to a groove of an auricle (e.g., a space connected to an ear canal) together with at least a portion of the housing 110. For example, the housing 110 can be shaped to fit in the concha part of the ear, while the movable member 120 can press against the helix part of the ear. According to an embodiment, the protrusion of the movable member 120, which protrudes to the outside of the housing 110, may be resized in such a manner of pushing the movable member 120 into the housing 110 or pulling the movable member 120 out of the housing 110.

When the ear wearable device 1 is worn on an ear, a first portion 111 of the housing 110 presses against the concha part of the ear and a second portion 112 of the housing 110 may be inserted into the ear canal. Referring to FIG. 2B, 2C, 2D, or 2E, in an embodiment, the first portion 111 of the housing 110 is convex in the first direction 11, and may be designed to include curved surfaces 1112 and 1113 that follow the surface of the concha part of the ear.

The second portion 112 of the housing 110 may be in the form of a cylinder protruding from the first portion 111.

The ear wearable device 1 may include a speaker (not illustrated) disposed in the inner space of the housing 110, and the sound generated from the speaker is transmitted to the outside through the opening 1121 (see FIG. 2F) formed in the second portion 112.

Figure 2:
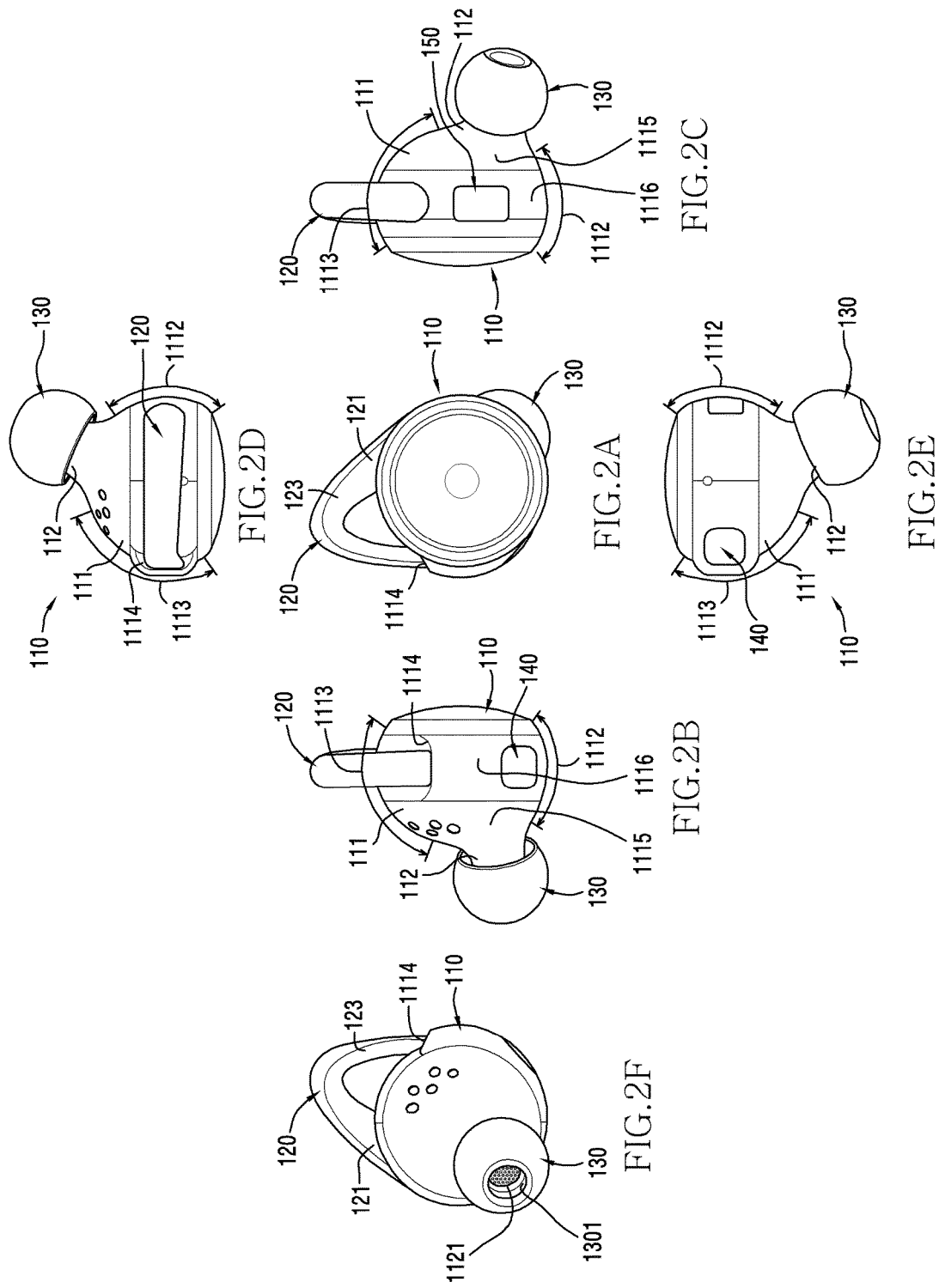
FIG. 2A, FIG. 2B, FIG. 2C, FIG. 2D, FIG. 2E and FIG. 2F are views illustrating appearances of the ear wearable device according to an embodiment viewed from various directions.

Referring to FIGS. 1 and 2, in an embodiment, the ear wearable device 1 may include an ear tip 130 coupled to the second portion 112 of the housing 110. The ear tip 130 may be a circular flexible member including a hollow portion 1301 (see FIG. 2F). When the ear wearable device 1 is worn on the ear, the ear tip 130 may be resiliently interposed between the inner surface of the ear canal and the outer circumferential surface of the second portion 112. According to various embodiments, the ear tip 130 is configured to be detachable and may be provided in plural number in various sizes.

Referring to FIGS. 1 and 2, in an embodiment, the movable member 120 may have a length extending from one end 121 to the other end (not illustrated). The first portion 111 of the housing 110 may include an opening 1114, and the movable member 120 may be installed to be movable inward or outward of the housing 110 through the opening 1114. The other end of the movable member 120 may be disposed in the housing 110, and an extension 123 connecting the one end 121 and the other end of the movable member 120 may be disposed to pass the opening 1114 of the housing 110. One end 121 of the movable member 120 may be fixed to the first portion 111 of the housing 110 at a position spaced away from the opening 1114, so that the movable member 120 coupled to the housing 110 may provide a protrusion 124 in the form of protruding (e.g., arc-shaped or curved) outward of the housing 110. According to an embodiment, the extension 123 of the movable member 120 may be pushed into the housing 110 or pulled out of the housing 110 through the opening 1114 of the housing 110, so that the protrusion 124 can be resized. The protrusion 124 of the movable member 120 may be used for attach the ear wearable device to the concha and helix of the ear (e.g., a space connected to the ear canal) together with at least a portion of the housing 110.

Although not illustrated, the groove of the auricle may include a concha directly connected to the ear canal, and a second space arranged after the first space in the outward direction (e.g., in the sixth direction 16 in FIG. 1). Referring to FIGS. 2B and 2C, in an embodiment, the first portion 111 of the housing 110 may include an A-surface 1115 corresponding to the shape of the concha, and a B-surface 1116 corresponding to the second space of the groove of the auricle. In an embodiment, the B-surface 1116 may include an outer circumferential surface or an outer circumference in the form of a ring. The position where the one end 121 of the movable member 120 is coupled to the housing 110 and the position of the opening 1114 of the housing 110, through which the extension 123 of the movable member 120 passes, may be disposed on the outer circumference of the B-surface 1116 to be spaced apart from each other. In an embodiment, the protrusion 124 of the movable member 120 may be designed to be convex in the fifth direction 15 (e.g., see FIG. 1) to generally support the inner surface of the second space of the groove of the auricle.

According to various embodiments, at least a portion of the protrusion 124 may be designed to include a flexible material. When the ear wearable device 1 is coupled to the ear, the protrusion 124 of the movable member 120 may resiliently support the inner surface of the groove of the auricle, whereby the coupling between the housing 110 and the groove of the auricle can be improved.

Referring to FIGS. 1 and 2, in an embodiment, the ear wearable device 1 may include a button 140 emerging from a hole 1111 formed in the first portion 111 of the housing 110. A portion 1401 of the button 140 may be exposed to the outside through the hole 1111 and may form a portion of the outer appearance of the ear wearable device 1. For example, the button 140 may be a member of a mechanism to be depressed or pushed when a user wants to change aspects, such as a length or a size, of the protrusion 124 of the movable member 120. According to an embodiment, the button 140 may be made of hard material, such as plastic or metal. When the button is pressed, the push member 140 may be in a pushed state moved inward of the housing 110. In an embodiment, referring to FIGS. 2B and 2E, the hole 1111 in which the button 140 is installed may be disposed on the B-surface 1116.

According to an embodiment, the ear wearable device 1 may include an elastic member disposed within the first portion 111 of the housing 110. The elastic member is able to elastically support and resist pushing of the button 140 so as to return the button 140 when an external force applied to the push member 140 is released.

According to an embodiment, the ear wearable device 1 may include a locking/unlocking device which enables the movement (e.g., push-in or pull-out) of the movable member 120 when the button 140 is pressed, and prevents or resists the movement of the movable member 120 when the button 140 is in the un-pushed state. According to an embodiment, when the button 140 is not pushed, the locking/unlocking device is able to make the movement of the movable member 120 by an external force difficult due to a coupling force (or a frictional force) between the button 140 and the extension 123 of the movable member 120. According to an embodiment, when the button 140 is pushed, the coupling force between the button 140 and the extension 123 of the movable member 120 may be released or decreased, and the locking/unlocking device may enable the movement (e.g., push-in or pull-out) of the movable member 120 by less external force.

According to an embodiment, the ear wearable device 1 illustrated in FIG. 1 and FIGS. 2A to 2F may be a device that is wearable on a right ear. Although not illustrated, an ear wearable device that is wearable on a left ear may be designed in a symmetrical structure with the ear wearable device 1 that is wearable on the right ear.

Figure 3:
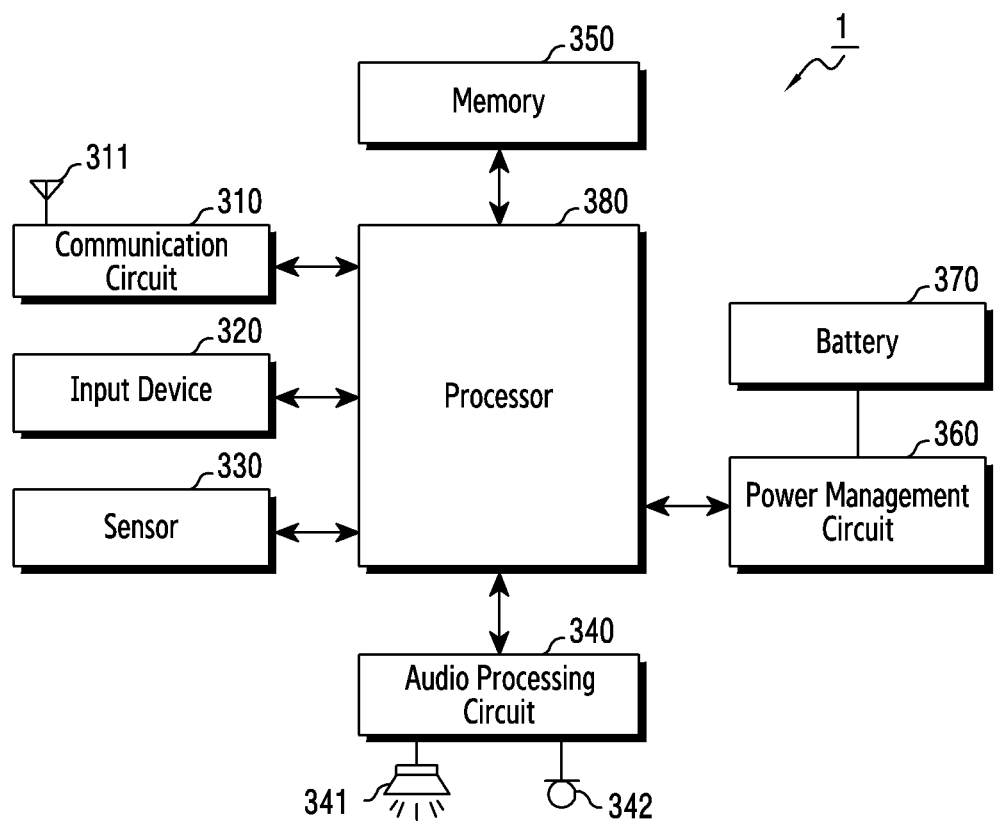
FIG. 3 is a block diagram of an ear wearable device according to an embodiment.

The ear wearable device 1 may include a plurality of electronic components disposed in the inner space of the housing 110. FIG. 3 is a block diagram of the ear wearable device 1 according to an embodiment. Referring to FIG. 3, the ear wearable device 1 may include an antenna 311, a communication circuit 310, an input device 320, a sensor 330, an audio processing circuit 340, a memory 350, a power management circuit 360, a battery 370, and a processor 380.

The antenna (or an antenna radiator) 311 may support various types of communication. According to an embodiment, the antenna 311 may support short range communication. The short-range communication may include at least one of, for example, Wireless Fidelity (Wi-Fi), Bluetooth, Near Field Communication (NFC), or Global Navigation Satellite System (GNSS).

According to various embodiments, the antenna 311 may support cellular communication. The cellular communication may use at least one of, for example, Long-Term Evolution (LTE), LTE Advance (LTE-A), Code Division Multiple Access (CDMA), Wideband CDMA (WCDMA), Universal Mobile Telecommunication System (UMTS), Wireless Broadband (WiBro), or Global System for Mobile communication (GSM).

According to various embodiments, the antenna 311 may include a radiator configured to support wireless charging (e.g., a wireless charging coil). The antenna 311 may be used for transmitting wireless power to an external device, or for wirelessly receiving power from an external device.

The antenna 311 may be various types of metallic members that are provided in the ear wearable device 1. According to an embodiment, the antenna 311 may be disposed within the housing 110 (e.g., see FIG. 1 or 2), or may form a portion of one surface of the housing 110. According to various embodiments, when the housing 110 (e.g., see FIG. 1 or 2) is formed of a metal, the antenna 311 may include a portion of the metal region or the entire metal region of the housing 110.

According to various embodiments, the antenna 311 may be mounted on a Printed Circuited Board (PCB) (not illustrated), on which the communication circuit 310 is mounted.

According to various embodiments, the communication circuit 310 may support wireless communication with an external device (e.g., a smart phone). According to various embodiments, the communication circuit 310 may support various types of communication using the antenna 311.

According to an embodiment, the communication circuit 310 may include various RF components between the antenna 311 and the processor 380. For example, in the reception of a wireless signal, the communication circuit 310 may receive the wireless signal from the antenna 311, may convert the received wireless signal into a baseband signal, and may transmit the converted baseband signal to the processor 380. The processor 380 may process the received baseband signal, and may control a human/mechanical interface of the ear wearable device 1 in correspondence to the received baseband signal. In the transmission of a wireless signal, the processor 380 may generate and output a baseband signal to the communication circuit 310. The communication circuit 310 may receive the baseband signal from the processor 380, may convert the received baseband signal into a wireless signal, and may transmit the wireless signal to the air through the antenna 311.

According to various embodiments, the communication circuit 310 may support wired communication with an external device. The communication circuit 310 may be electrically connected to at least one contact disposed on the outer surface of the housing 110 (e.g., see FIG. 1). When the ear wearable device 1 is mounted on a mounting portion of an external electronic device, the at least one contact of the ear wearable device 1 may be electrically connected to at least one contact provided in the mounting portion of the external electronic device.

According to various embodiments, the communication circuit 310 may support the reception of audio data (or audio contents) from an external electronic device (e.g., a server, a smart phone, a PC, a PDA, or an access point). According to various embodiments, the communication circuit 310 may support transmission of audio data to an external device (e.g., another ear wearable device).

The input device 320 may be configured to generate various input signals that are necessary to operate the ear wearable device 1. The input device 320 may include a touch pad, a touch panel, a button, or the like. The touch pad may recognize a touch input in at least one of, for example, a capacitive type, a pressure-sensitive type, an infrared type, or an ultrasonic type. When a capacitive-type touch pad is provided, it may be possible to recognize a physical contact or proximity. The touch pad may further include a tactile layer. The touch panel including the tactile layer may provide a tactile response to the user. The button may include, for example, a physical button or an optical key.

According to various embodiments, the input device 320 may generate a user input relating to ON or OFF of the ear wearable device 1. According to various embodiments, the input device 320 may generate a user input relating to a communication (e.g., short range communication) connection between the ear wearable 1 and an external device.

According to an embodiment, the input device 320 may generate a user input associated with audio data (or audio contents). For example, the user input may be associated with functions of, for example, reproduction start, reproduction pause, reproduction stop, reproduction speed control, reproduction volume control, and mute of audio data.

In an embodiment, referring to FIG. 1, the ear wearable device 1 may include a touch pad (not illustrated) disposed along a surface 1117 facing the sixth direction 16. When the ear wearable device 1 is worn on the ear, the surface 1117 on which the touch pad is installed is directed to a side of the ear, and then the gesture input on the touch pad using a finger can be performed in the state in which the ear wearable device 1 is worn.

In certain embodiments, surface 1117 can be used to control play, pause, etc. functions, as well as the volume. The operation of the ear wearable device 1 may be controlled by various gestures such as tapping or swiping up and down on the surface 1117 on which the touch pad is installed. According to an embodiment, when a gesture is detected for a single tap through the surface 1117, the ear wearable device 1 (or processor 380) may reproduce audio data or may pause the reproduction. According to an embodiment, when a gesture relating to two taps is sensed through the surface 1117, the ear wearable device 1 may switch its reproduction to the next audio data. When a gesture relating to three taps is detected through the surface 1117, the ear wearable device 1 may switch its reproduction to previous audio data. According to various embodiments, when a gesture of swiping up or down through the face 1117 is sensed, the ear wearable device 1 may control the volume associated with the reproduction of the audio data.

According to various embodiments, when a gesture of two taps is detected through the surface 1117 when a call is received, the ear wearable device 1 may connect the phone.

The sensor 330 may measure a physical amount or may sense the operating state of the ear wearable device 1. The sensor 330 may convert the measured or sensed information into an electric signal. The sensor 330 may include, for example, an acceleration sensor, a gyro sensor, a geomagnetic field sensor, a magnetic sensor, a proximity sensor, a gesture sensor, a grip sensor, or a biometric sensor.

Referring again to FIG. 2C, in an embodiment, the ear wearable device 1 may include an optical sensor aligned with a light-transmissive region 150 of the B-surface 1116 of the housing 110. The optical sensor may include a light-emitting unit (e.g., an LED) that outputs light in at least one wavelength band. The optical sensor may include a light-receiving unit (e.g., a photodiode) that receives light in one or more wavelength bands scattered or reflected from an object so as to generate an electrical signal.

Referring to FIG. 3 again, in an embodiment, the processor 380 may transmit an electrical signal from the light-receiving unit to an external device (e.g., a smart phone) using the communication circuit 310. The external device may analyze the electrical signal acquired from the ear wearable device 1 and acquire information relating to the corresponding detection mode (e.g., a proximity detection mode or a biometric detection mode). In certain embodiments, the processor 310 can detect user's body temperature using the light-receiving unit. According to an embodiment, in a heartbeat detection mode, the external device may determine the heart rate based on the electrical signal transmitted from the light-receiving unit.

According to various embodiments, the processor 380 may analyze the electrical signal from the light-receiving unit so as to acquire information relating to the corresponding detection mode (e.g., a proximity detection mode or a biometric detection mode). The processor 380 may transmit the acquired information to the external device using the communication circuit 310. The processor 380 may output the acquired information through the speaker 341.

According to various embodiments, the sensor 330 may detect information or a signal as to whether the ear wearable device 1 is coupled to the ear.

According to various embodiments, the sensor 330 may detect information or a signal as to whether the ear wearable device 1 is coupled to an external device (e.g., a charging device).

According to various embodiments, although not illustrated, the ear wearable device 1 may include a detection target member corresponding to a sensor of an external device (e.g., a charging device). For example, the external device may include a Hall IC installed in a mounting portion, and the ear wearable device 1 may include a magnet. When the ear wearable device 1 is coupled to the mounting portion of the external device, the Hall IC of the external device may recognize the magnet installed in the ear wearable device 1 and may output a signal relating to the coupling of the external device and the ear wearable device 1. In another example, the external device may include a contact disposed on the mounting portion, and the ear wearable device 1 may include a contact disposed on the housing 110 (see FIG. 1). When the ear wearable device 1 is coupled to the mounting portion of the external device, the contact of the external device and the contact of the ear wearable device 1 may be electrically connected to each other and the external device may recognize the coupling of the ear wearable device 1.

The audio processing circuit 340 may support an audio data collection function. The audio processing circuit 340 may reproduce collected audio data. According to an embodiment, the audio processing circuit 340 may include an audio decoder (not illustrated) and a D/A converter (not illustrated). The audio decoder may convert audio data stored in the memory 350 into a digital audio signal. The D/A converter may convert the digital audio signal, which has been converted by the audio decoder, into an analog audio signal. According to various embodiments, the audio decoder may convert audio data, which has received from an external device (e.g., a server, a smart phone, a PC, a PDA, or an access point) through the communication circuit 310 and stored in the memory 350, into a digital audio signal. The speaker 341 may output the analog audio signal converted by the D/A converter.

According to an embodiment, the audio processing circuit 340 may include an A/D converter (not illustrated). The A/D converter may convert an analog sound signal delivered through the microphone 342 into a digital sound signal.

According to various embodiments, the audio processing circuit 340 may reproduce various audio data set in the operating action of the ear wearable device 1. For example, when it is sensed that the ear wearable device 1 is coupled to the ear or separated from the ear, the audio processing circuit 340 may be designed to reproduce audio data relating to the corresponding effect or guide sound. According to various embodiments, when it is sensed that the ear wearable device 1 is coupled to an external device (e.g., a charging device), or when it is sensed that the ear wearable device 1 is separated from the external device, the audio processing circuit 340 may be designed to reproduce audio data relating to the corresponding effect or guide sound. The output of effect sound or guide sound may be omitted according to the user's setting or the designer's intention. According to various embodiments, the audio processing circuit 340 may also be designed to be included in the processor 380.

The memory 350 may store, for example, data, applications, and algorithms, which correspond to various operation systems required for operating the ear wearable device 1 or various user functions. The memory 350 may include at least one high speed random accessory memory (e.g., a magnetic disc storage device) and/or a non-volatile memory or at least one optical storage device and/or a flash (e.g., NAND or NOR).

According to an embodiment, the memory 350 may include a non-volatile memory that stores first audio data (non-volatile audio data) received from an external electronic device (e.g., a server, a smart phone, a PC, a PDA, or an access point). According to various embodiments, the memory 350 may include a volatile memory that stores second audio data (volatile audio data) received from an external device.

The power management circuit 360 (e.g., Power Management Integrated Circuit (PMIC)) may effectively manage and optimize the use of power of the battery 370 within the ear wearable device 1. According to an embodiment, in accordance with to a load to be processed, the processor 380 may transmit a signal according to the load to the power management circuit 360. The power management circuit 360 may adjust the power to be supplied to the processor 380.

The power management circuit 360 may include a battery charging circuit. According to an embodiment, when the ear wearable device 1 is coupled to an external device, the power management circuit 360 may charge the battery 370 by receiving power provided from the external device.

According to various embodiments, the power management circuit 360 may include a wireless charging circuit. The wireless charging circuit may wirelessly receive power from the external device via the antenna 341 and may charge the battery 370 using the received power.

According to various embodiments, the ear wearable device 1 may include a display device (not illustrated). The ear wearable device 1 may be configured to provide various screen interfaces required for operating the ear wearable device 1. The display device may provide a user interface relating to the reproduction of audio data. According to various embodiments, the display device may provide a user interface relating to a function of receiving audio data from an external device or a function of transmitting audio data to the external device.

According to various embodiments, the display device may include a light-emitting means such as a light-emitting diode (LED). For example, the light-emitting means may be controlled to emit light having a color corresponding to under-charging or completion of charging. For example, when the ear wearable device 1 is connected in communication to an external device (e.g., a smart phone or a web server), the light-emitting means may be controlled to emit light having a specific color. For example, in accordance with the reproduction state of audio data (e.g., under-reproduction or reproduction pause), the light-emitting means may be controlled to emit light having a specific color. For example, according to a user input generated through the input device, the light-emitting means may be controlled to generate light having a specific color.

According to various embodiments, the processor 380 may be configured to control various signal flows, information collection, output, and the like rated to audio data.

The processor 380 may support various operations based on at least a portion of the user input from the input device 320. According to an embodiment, the processor 380 may turn ON or OFF the ear wearable device 1 according to the user input. According to an embodiment, the processor 380 may connect the ear wearable device 1 in communication to an external device according to the user input. According to an embodiment, the processor 380 may receive audio data from an external device or transmit audio data to an external device in accordance with the user input. According to an embodiment, processor 380 may reproduce audio data or control the reproduction in accordance with the user input (e.g., reproduction start, reproduction pause, reproduction stop, reproduction speed control, reproduction volume control, and mute of audio data).

The processor 380 is designed to receive audio data from an external device (e.g., a server, a smart phone, a PC, a PDA, or an access point) via the communication circuit 310 and to store the received audio data in the memory 350. According to an embodiment, the processor 380 may receive non-volatile audio data (or download audio data) from an external device and may store the received non-volatile audio data in a non-volatile memory. According to various embodiments, the processor 380 may receive volatile audio data (or streaming audio data) from an external device and may store the received volatile audio data in a volatile memory.

According to an embodiment, the processor 380 may reproduce audio data (e.g., non-volatile audio data or volatile audio data) stored in the memory 350 and may output the reproduced audio data through the speaker 341. The processor 380 may decode the audio data so as to acquire an audio signal (audio data reproduction). The processor 380 may output the acquired audio signal through the speaker 341.

According to various embodiments, the processor 380 may receive an audio signal from an external device and output the received audio signal through the speaker 341. An external device (e.g., an audio reproduction device) may decode audio data so as to acquire an audio signal (audio data reproduction). The external device may transmit the acquired audio signal to the ear wearable device 1. The processor 380 may perform various operations based on at least a portion of the information acquired from the sensor 330. According to an embodiment, the processor 380 may determine, from the information acquired from the sensor 330, whether or not the ear wearable device 1 is worn on the ear. When it is determined that the ear wearable device 1 is worn on the ear, the processor 380 may reproduce the audio data stored in the memory 350 according to the user input for audio data reproduction, and may output the reproduced audio data to the speaker 341.

According to various embodiments, when it is determined that the ear wearable device 1 is not worn on the ear in a mode in which the ear wearable device 1 receives audio data from an external device, reproduces the audio data, and outputs the reproduced audio data to the speaker 341, the processor 380 may stop the mode or may transmit a signal related thereto to the external device. The external device may receive a signal related to the state in which the ear wearable device 1 is not worn on the ear and may stop transmission of audio data to the ear wearable device 1.

According to various embodiments, when it is determined that the ear wearable device 1 is not worn on the ear in a mode in which the ear wearable device 1 receives an audio signal from an external device and outputs the audio signal to the speaker 341, the processor 380 may stop the mode or may transmit a signal related thereto to the external device. The external device may receive a signal related to the state in which the ear wearable device 1 is not worn on the ear, and may stop the reproduction of audio data and transmission of an audio signal.

According to various embodiments, when it is determined that the ear wearable device 1 is worn on the ear, the processor 380 may activate a biometric sensor (e.g., a heart rate sensor). When it is determined that the ear wearable device 1 is not worn on the ear, the processor 380 may deactivate the biometric sensor.

According to various embodiments, when the ear wearable device 1 is connected in communication to another ear wearable device, the ear wearable device 1 may become a master device and the other ear wearable device may become a slave device. According to an embodiment, the ear wearable device 1 serving as the master device may not only output an audio signal received from the external device to the speaker 341, but also transmit the audio signal to other ear wearable devices.

According to various embodiments, the ear wearable device 1 may provide a sound recognition function that generates a sound command from an analog sound signal received using the microphone 342. The sound command may be related to an input for supporting, for example, the reception, transmission, or reproduction of audio data.

According to various embodiments, the ear wearable device 1 may further include various modules according to a provided type thereof. Variations are not all enumerated since the variations are very diverse according to the convergence trend of the digital device, but the components equivalent to the above-mentioned components may be further included in the ear wearable device 1. According to an embodiment, in the ear wearable device 1, specific components may be omitted from the above-mentioned components or may be replaced by other components according to the provided type of the electronic device 700. This may be easily understood by a person ordinarily skilled in this technical field.

Figure 4:
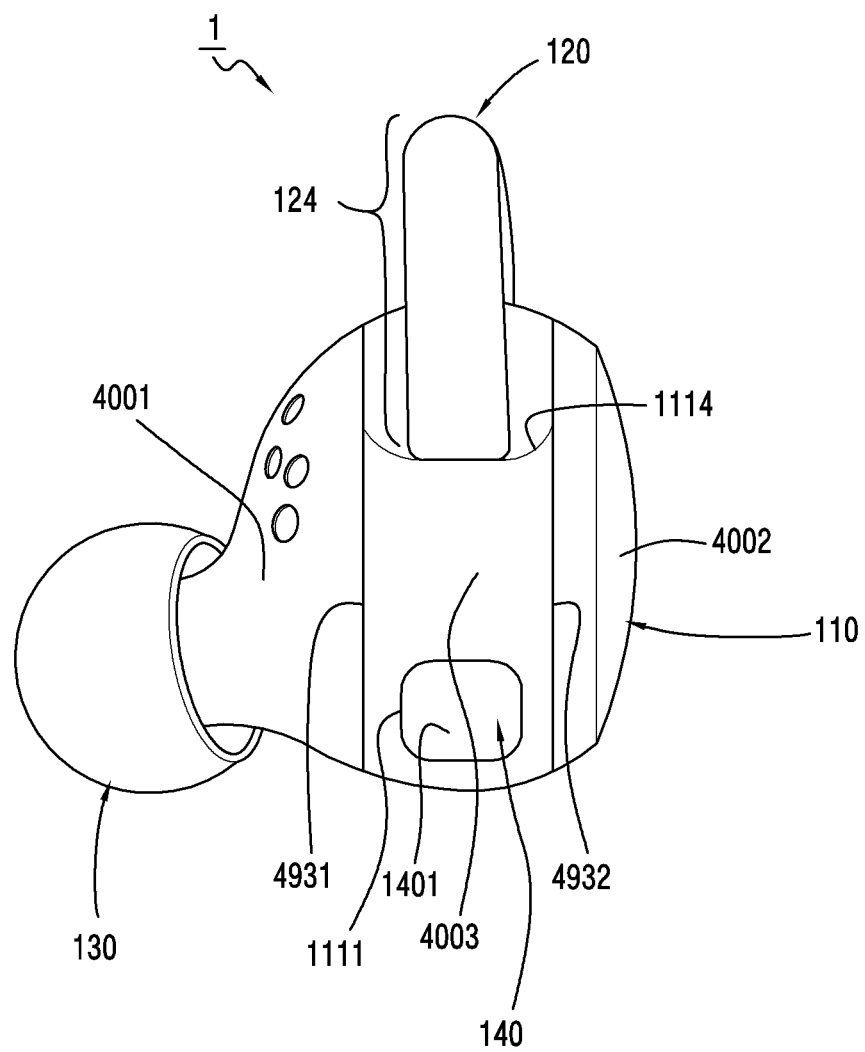
FIG. 4 is a side view of the ear wearable device according to an embodiment.
Figure 5A:
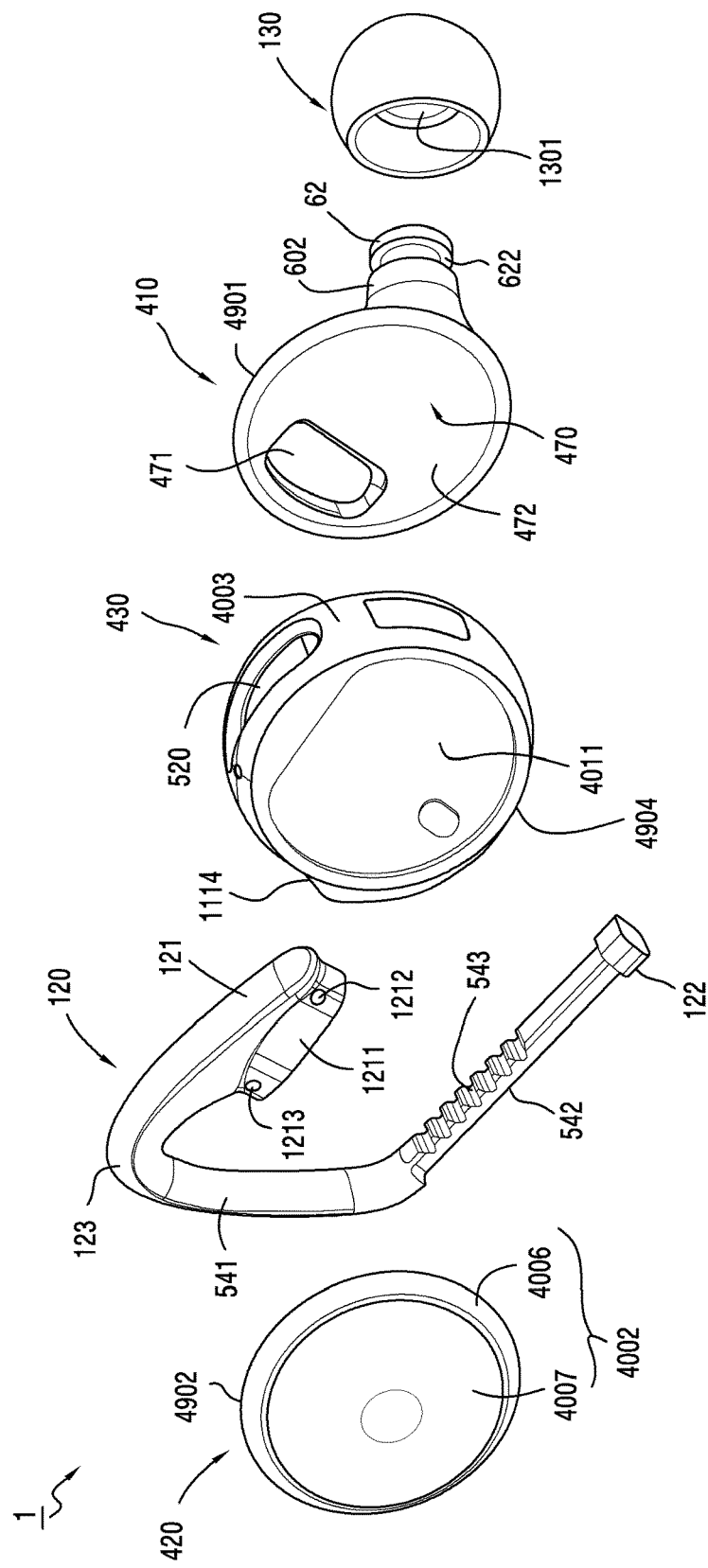
FIG. 5A and FIG. 5B are exploded views of the ear wearable device according to an embodiment.
Figure 5B:
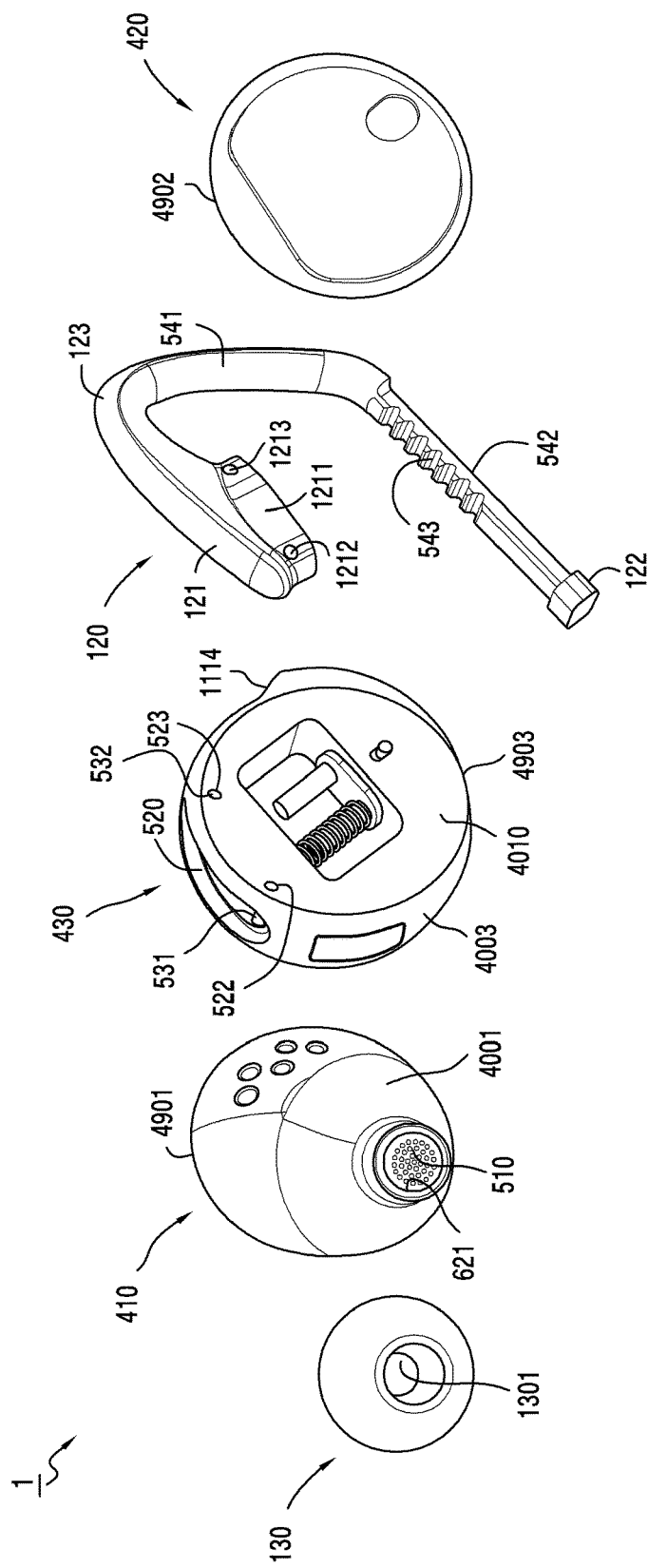
Figure 6:
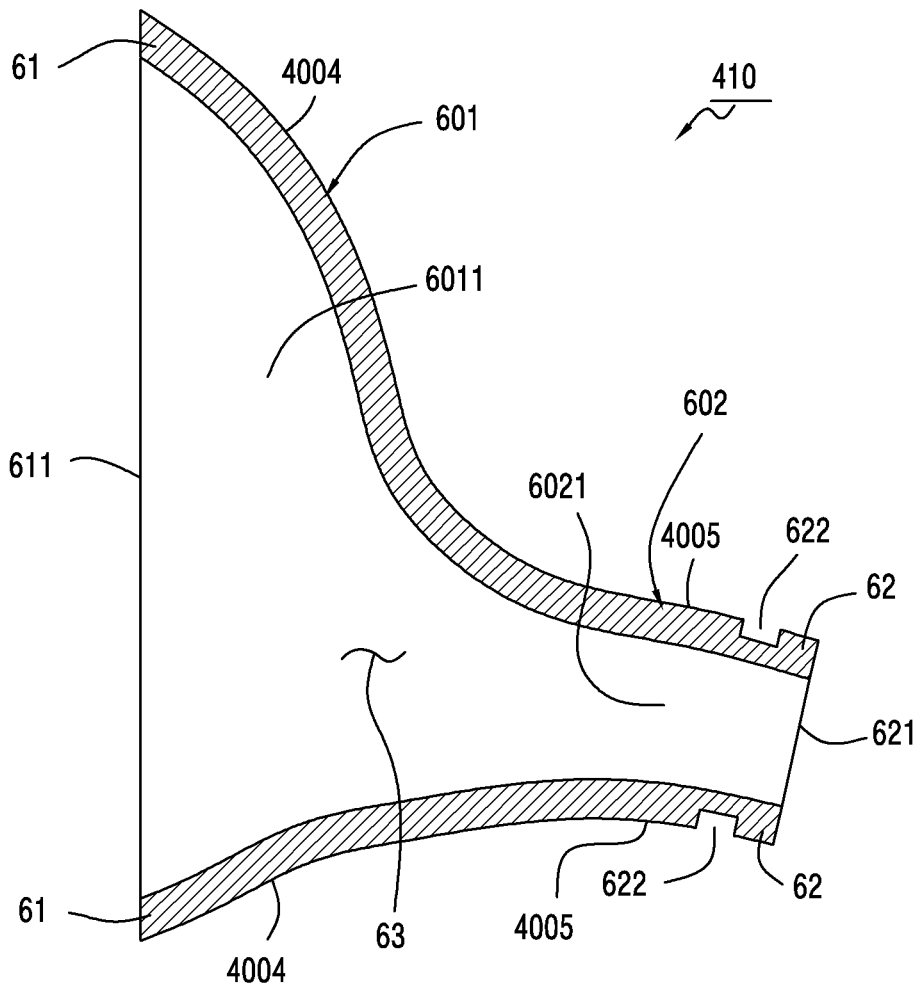
FIG. 6 is a cross-sectional view of a first housing forming a portion of the external appearance of the ear wearable device in an embodiment.
Figure 7:
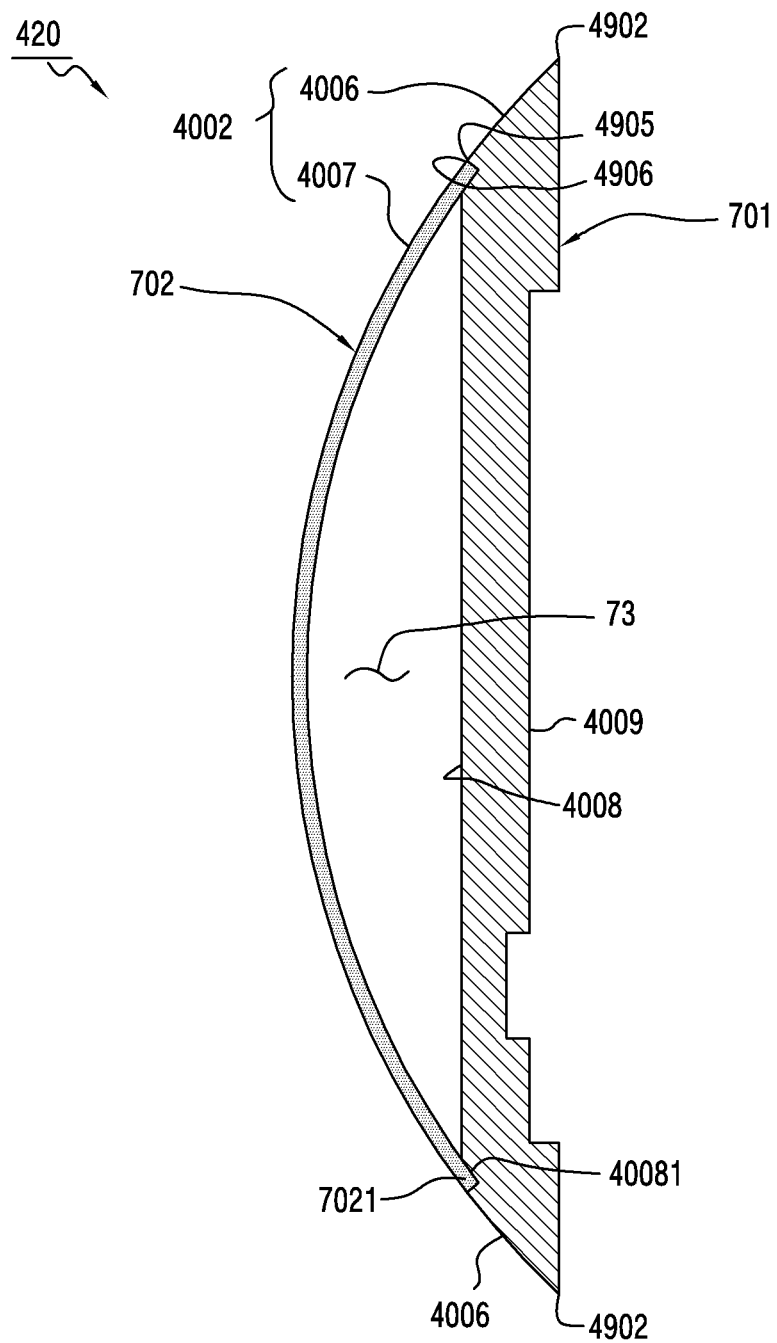
FIG. 7 is a cross-sectional view of a second housing forming a portion of the external appearance of the ear wearable device in an embodiment.
Figure 8A:
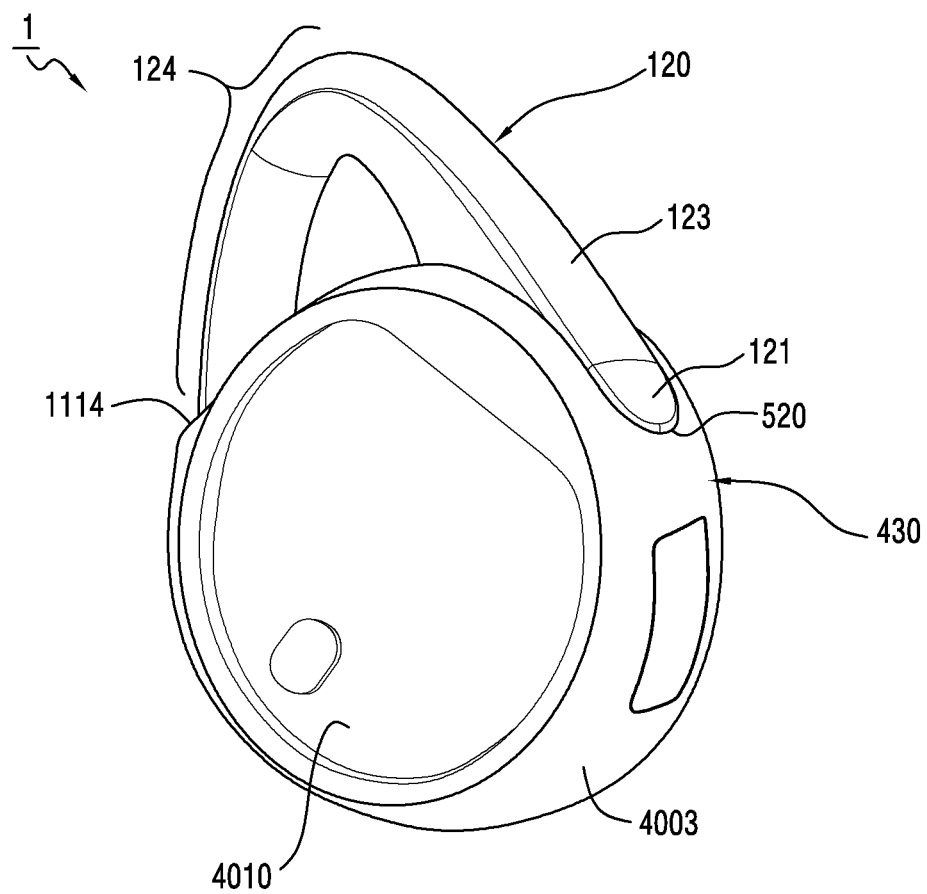
FIG. 8A and FIG. 8B are views illustrating a state in which a movable member, which is movable inward or outward of a housing, is coupled to a third housing forming a portion of the external appearance of the ear wearable device in an embodiment.
Figure 8B:
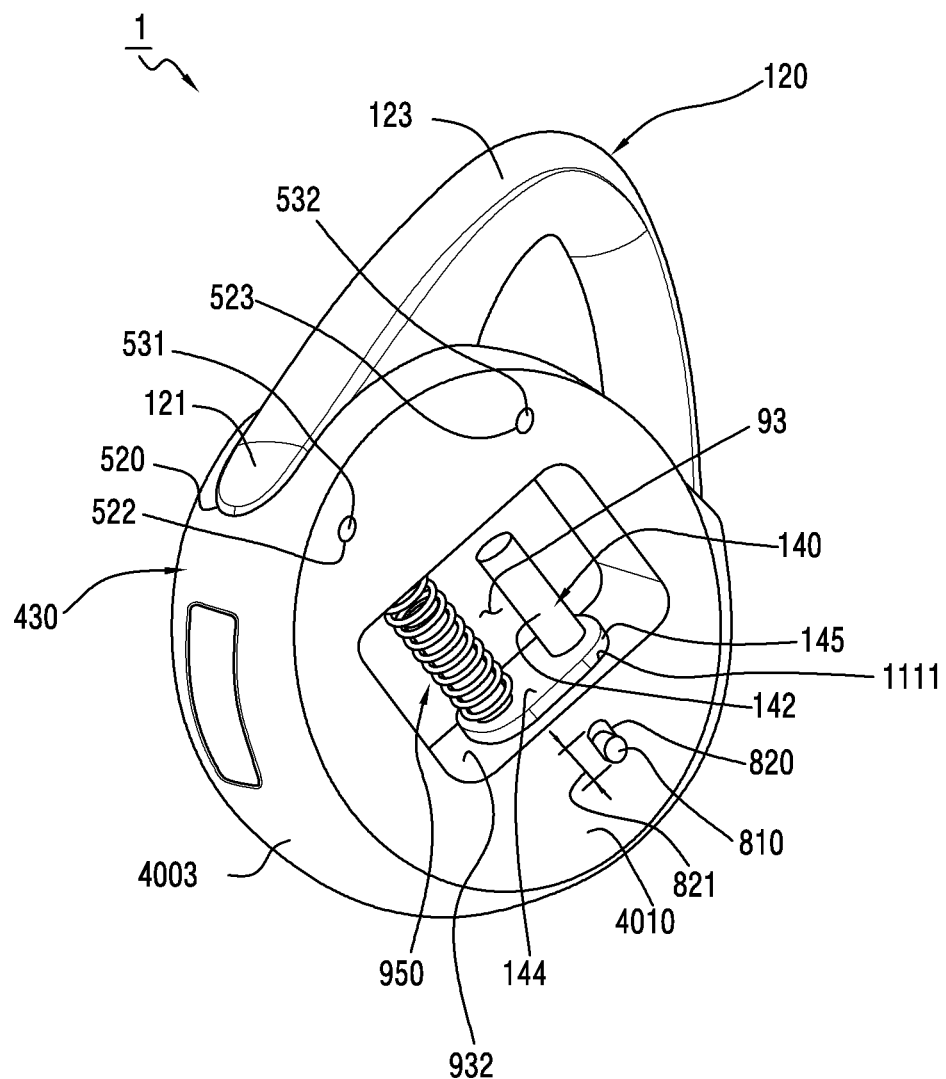
Figure 9A:
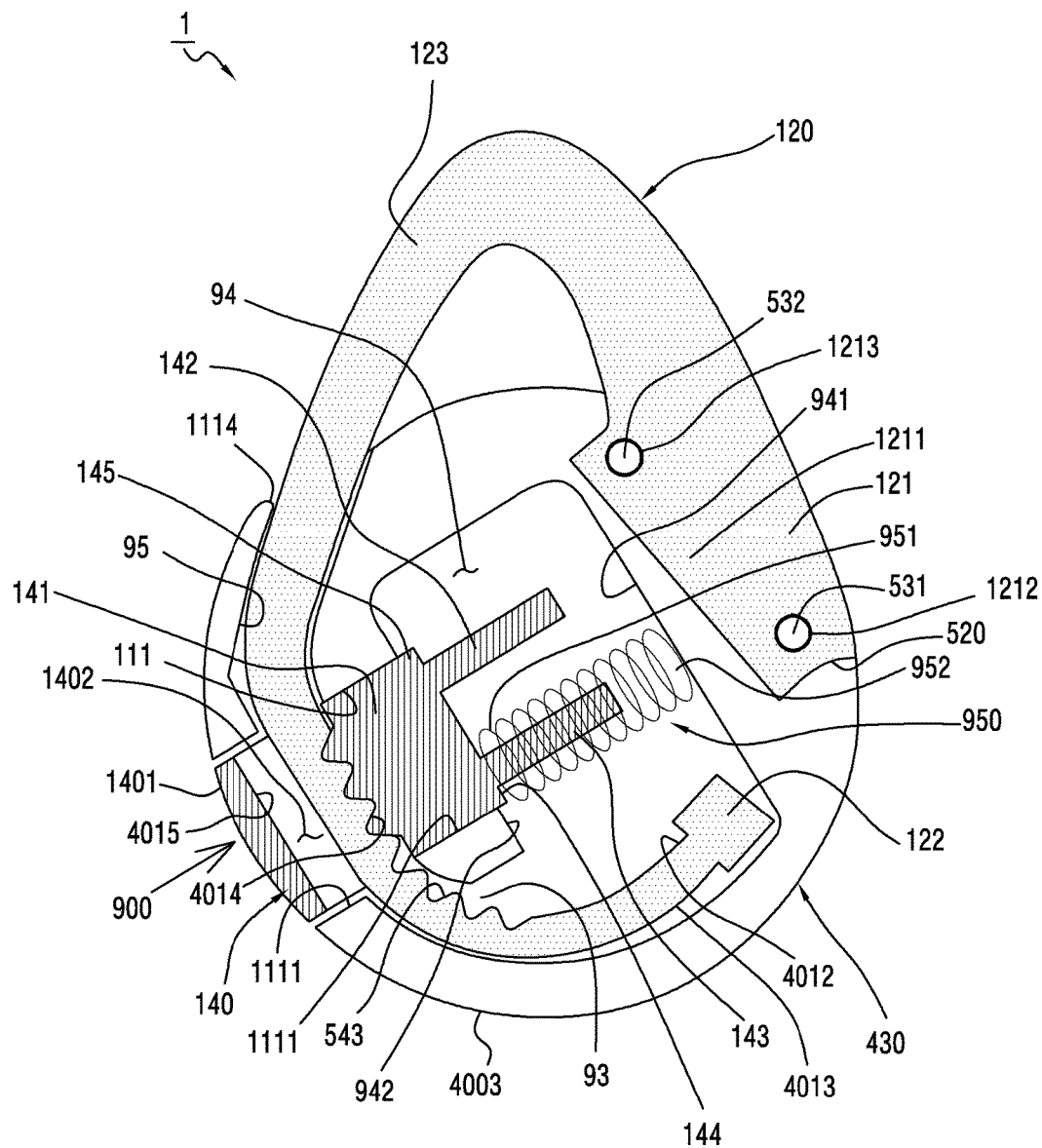
FIG. 9A and FIG. 9B are cross-sectional views for explaining a locking/unlocking device for locking or unlocking the movement of the movable member in an embodiment.
Figure 9B:
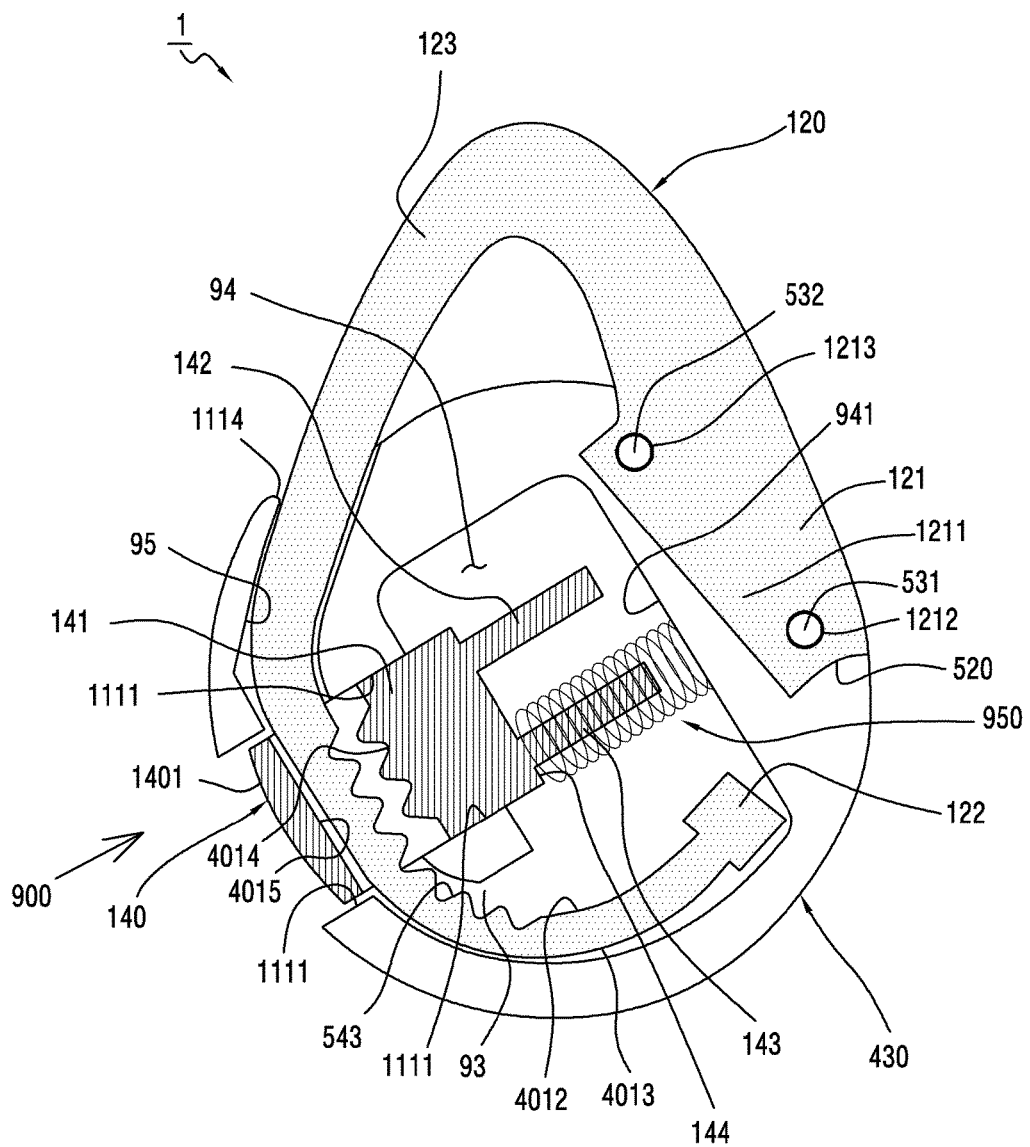

FIG. 4 is a side view of the ear wearable device according to an embodiment. FIGS. 5A and 5B are exploded views of the ear wearable device according to an embodiment. FIG. 6 is a cross-sectional view of a first housing forming a portion of the external appearance of the ear wearable device in an embodiment. FIG. 7 is a cross-sectional view of a second housing forming a portion of the external appearance of the ear wearable device in an embodiment. FIGS. 8A and 8B are views illustrating a state in which a movable member, which is movable inward or outward of a housing, is coupled to a third housing forming a portion of the external appearance of the ear wearable device in an embodiment. FIGS. 9A and 9B are cross-sectional views for disclosing a locking/unlocking device for locking or unlocking the movement of the movable member in an embodiment.

Referring to FIG. 4, the ear wearable device 1 may include a housing 110 that forms the entirety or at least a portion of the external appearance thereof. According to various embodiments, the housing 110 may be formed entirely of a single material or a combination of multiple materials. According to various embodiments, the housing 110 may include a non-metallic material or a metallic material. According to various embodiments, the housing 110 may be formed of materials such as a plastic, a metal, carbon fibers, other fiber composites, ceramics, glass, wood, or combinations thereof.

According to an embodiment, the housing 110 may form an external appearance including a first surface 4001, a second surface 4002, and a third surface 4003. The first surface 4001 and the second surface 4002 may be surfaces disposed on the opposite sides of the housing 110, respectively, and the third surface 4003 may be a surface surrounding a space between the opposite sides of the housing 110.

Referring to FIGS. 5A and 5B, in an embodiment, the housing 110 may include a first housing 410 forming the first surface 4001, a second housing 420 forming the second surface 4002, and a third housing 430 forming the third surface 4003. The third housing 430 may be disposed between the first housing 410 and the second housing 420, and the first housing 410 and the second housing 420 are coupled to each other through the third housing 430.

The first surface 4001 of the first housing 410 may include a first edge 4901, and the second surface 4002 of the second housing 420 may include a second edge 4902. The third surface 4003 of the third housing 430 may include a third edge 4903 that is in contact with the first edge 4901 along the first edge 4901. The third surface 4003 of the third housing 430 may include a fourth edge 4904 that is in contact with the second edge 4902 along the second edge 4902. According to an embodiment, when the first housing 410 and the third housing 430 are coupled to each other, the first surface 4001 and the third surface 4003 may be smoothly connected to each other. When the second housing 420 and the third housing 430 are coupled to each other, the second surface 4002 and the third surface 4003 may be smoothly connected to each other.

Referring to FIG. 4 again, a first boundary 4931 between the first surface 4001 and the third surface 4003 (e.g., a junction of the first edge 4901 and the third edge 4903 in FIG. 5B) and a second boundary 4932 between the second surface 4002 and the third surface 4003 (e.g., the junction of the second edge 4902 and the fourth edge 4904 in FIG. 5A) may form a closed curve on a two-dimensional or three-dimensional space. The third surface 4003 may be an annular surface disposed between the first boundary 4931 and the second boundary 4932.

The movable member 120 can be disposed inside the third housing 430 and protrude from hole 520.

According to an embodiment, the first boundary 4931 may be in the form of a circle on a first plane (not illustrated), the second boundary 4932 may be in the form of a circle on a second plane (not illustrated), and the third surface 4003 may be a circular-annular surface. The first plane may be spaced apart from the second plane in a direction perpendicular to the second plane, and may be parallel to the second plane. According to various embodiments, although not illustrated, the first plane may be designed to form an acute angle with the second plane.

According to various embodiments, although not illustrated, the first boundary 4931 or the second boundary 4932 may be in the form of a simple closed curve of various shapes other than a circle or various sizes. For example, although not illustrated, the first boundary 4931 and the second boundary 4932 may be designed in a substantially triangular shape, and the third surface 4003 may be a triangular-annular surface.

Referring to FIG. 6, the first housing can be configured to enter the auditory canal when the ear wearable device 1 is inserted into the ear. The first housing 410 has a tubular structure including a first opening 611 formed in a first end portion 61 and a second opening 621 formed in a second end portion 62. According to an embodiment, the first housing 410 may have a structure in which the inner space 63 is narrowed toward the second opening 621. According to an embodiment, the first housing 410 may include a 1-1 part 601 having the first end portion 61 and a 1-2 part 602 having the second end portion 62. The 1-1 part 601 may be in the form of a convex cover coupled to the third housing 430. The 1-2 part 602 may be in the form of a cylinder extending from the 1-1 part 601. The inner space 6011 of the 1-1 part 601 and the inner space 6021 of the 1-2 part 602 are connected to each other, and the first housing 410 may provide the first inner space 63 including the inner spaces 6011 and 6021.

According to an embodiment, the first surface 4001 (see FIG. 4 or FIG. 5B) of the first housing 410 is divided into a surface 4004 included in the 1-1 part 601 and a surface 4005 included in the 1-2 part 602, and the surface 4004 and the surface 4005 may be smoothly connected to each other. When the ear wearable device 1 is worn on the ear, the 1-1 part 601 is coupled to the groove of the auricle, such as the concha of the ear (e.g., the space connected to the ear canal), and the 1-2 part 602 may be inserted into the auditory canal. At least a portion of the surface 4004 is designed to include a curved surface following the surface of the concha of the ear, whereby the coupling between the 1-1 part 601 and the groove of the auricle can be improved.

According to various embodiments, at least a portion of the surface 4004 of the first housing 410 may be designed to include a flexible material. When the first housing 410 is placed against the concha of the ear (e.g., the space connected to the ear canal), at least a portion of the surface 4004, which includes the flexible material, elastically supports the concha of the ear, whereby the coupling between the housing 110 and the ear can be improved.

Referring to FIGS. 5B and 6, sound generated from a speaker 341 (e.g., see FIG. 3) disposed in the housing 110 may be emitted to the outside through the second opening 621 of the first housing 410. According to an embodiment, a circuit (not illustrated) including a speaker 341 (e.g., see FIG. 3) may be disposed in a first inner space 63. Referring to FIG. 3 again, the communication circuit 310, the audio processing circuit 340, the power management circuit 360, and the like of FIG. 3 may be mounted on a PCB. The PCB, a battery 370 (e.g., see FIG. 3), and the like may be disposed in the inner space (not illustrated) of the third housing 430. According to an embodiment, the ear wearable device 1 may include an electrical connection means (e.g., an FPCB) (not illustrated) that connects the circuit including the speaker 341 and disposed in the first inner space 63 and the PCB disposed in the third housing 430.

Referring to FIGS. 5A and 6, in various embodiments, the ear wearable device 1 may include a plate 470 coupled to the first opening 611 of the first housing 410. By the coupling between the first housing 410 and the plate 470, a separate first inner space 63 may be formed.

According to various embodiments, the plate 470 may include an opening 471, and an electrical connection means may be disposed through the opening 471.

Referring to FIGS. 5A and 6, in various embodiments, the circuit including the speaker 341 disposed in the first inner space 63 may include at least one first contact (not illustrated) disposed on a surface 472 of the plate 470. Referring to FIG. 5B again, the third housing 430 may include at least one second contact (not illustrated) disposed on surface 4010. When the first housing 410 and the third housing 430 are coupled to each other, the first and second contacts can be electrically connected to each other. According to various embodiments, the first contact or the second contact may include a flexible conductive member. For example, the flexible conductive member may include a C-clip, a pogo-pin, a spring, a conductive balloon and rubber, a conductive tape, a cooper connector, or the like.

Referring to FIG. 5B, in various embodiments, the ear wearable device 1 may include a porous member 510 disposed in the second opening 621. The porous member 510 is able to pass sound output from the ear wearable device 1 and to prevent foreign matter from flowing into the inside of the housing 110.

Referring to FIGS. 4, 5A, 5B, and 6, the ear wearable device 1 may include an ear tip 130 coupled to the 1-2 part 602 (see FIG. 6). According to an embodiment, the ear tip 130 may be a circular flexible member including a hollow portion 1301. The second end 62 of the 1-2 part 602 may include a groove 622 (see FIG. 6) formed along the outer circumference, and the ear tip 130 may be coupled to the groove 622. When the ear wearable device 1 is worn on the ear, the ear tip 130 is elastically interposed between the inner surface of the ear canal and the outer circumferential surface (the fifth surface 4005 in FIG. 6) of the 1-2 part 602 (see FIG. 6).

Referring to FIGS. 4 and 5A, the second surface 4002 may include a convex curved surface. Referring to FIG. 7, in an embodiment, the second surface 4002 may include a dome-shaped surface 4007 and an annular (e.g., circular-annular) surface 4006 that is smoothly connected to the surface 4007.

Referring to FIGS. 5A, 5B, and 7, according to an embodiment, the second housing 420 may include a plate-shaped 2-1 part 701 including opposite surfaces (e.g., an side 4008 and a ninth side 4009). The second edge 4902 may be a boundary between the surface 4006 and the surface 4009. The 2-1 part 701 may include edge 4905 which is a boundary between the surface 4006 and the surface 4008. The second housing 420 may include a 2-2 part 702 coupled to the 2-1 part 701, and the 2-2 part 702 may include the face 4007. The surface 4007 may include a edge 4906 that is in contact with the edge 4905 of the surface 4006 along the edge 4905.

According to an embodiment, the 2-2 part 702 may be in the form of a convex cover (e.g., arc-shaped or dome-shaped plate). The surface 4008 of the 2-1 part 701 may include an installation portion (e.g., a groove) 40081 to which the end portion 7021 of the 2-2 part 702 is coupled in the vicinity of the edge 4905. According to various embodiments, the end portion 7021 of the 2-2 part 702 may be coupled to the installation portion 40081 of the 2-1 part 701 using various means such as an adhesive material. When the 2-1 part 701 and the 2-2 part 702 are coupled to each other, a inner space 73 may be formed between the 2-1 part 701 and the 2-2 part 702.

According to an embodiment, an input device (e.g., the input device 320 of FIG. 3) (e.g., a touch pad) may be disposed in the second inner space 73. The ear wearable device 1 may include an electrical connection means (e.g., an FPCB) (not illustrated) that electrically connects an input device disposed in the second inner space 73 and the PCB disposed in the third housing 430.

Referring to FIGS. 5B and 7, in various embodiments, although not illustrated, the 2-1 part 701 of the second housing 420 may include an opening, and the electrical connection means may be arranged to pass through the opening.

Referring to FIGS. 5A and 7, an input device (e.g., a touch pad) (not illustrated) disposed in the second inner space 73 may include at least one third contact (not illustrated) disposed on the surface 4009 of the 2-1 part 701. The third housing 430 may include at least one contact (not illustrated) disposed on surface 4011. When the second housing 420 and the third housing 430 are coupled to each other, the third and fourth contacts can be electrically connected to each other. According to various embodiments, the third or fourth contact may include a flexible conductive member (e.g., a C-clip, a pogo pin, a spring, a conductive ball, rubber, conductive tape, or a cooper connector).

Referring to FIGS. 5A and 5B, the third housing 430 may include surface 4010 including at least a portion to which the first housing 410 is coupled. The third housing 430 may include an surface 4011 including at least a portion to which the second housing 420 is coupled. The coupling between the first housing 410 and the surface 4010 or the coupling between the second housing 420 and the surface 4011 may be formed using various means such as an adhesive material, a bolt, and a snap-fit. According to an embodiment, the third housing 430 may be generally cylindrical in shape, and the surface 4010 and the surface 4011 may be disposed opposite each other.

When the ear wearable device 1 is worn on the ear, the third housing 430 is coupled to a concha of the ear (e.g., a space connected to the ear canal) (not illustrated), and at least a portion of the third surface 4303 of the third housing 430 may be brought into contact with the surface of the groove of the auricle. According to various embodiments, at least a portion of the third surface 4003 may be designed to include a flexible material. When the ear wearable device 1 is coupled to the ear, at least a portion of the third surface 1003 including the flexible material may resiliently support the inner surface of the groove of the auricle, whereby the coupling between the housing 110 and the groove of the auricle can be improved.

Referring to FIGS. 4, 5A, 5B, 8A, 8B, 9A, and 9B, the ear wearable device 1 may include a movable member 120 coupled to the third housing 430 to be movable inward or outward of the third housing 430. According to an embodiment, the protrusion 124 (see FIG. 4 or FIG. 8A) of the movable member 120, which protrudes to the outside of the third surface 4003, may be resized in such a manner of pushing the movable member 120 into the third housing 430 or pulling the movable member 120 out of the third housing 430.

Referring to FIGS. 4, 5A, 5B, 8A, 8B, 9A, and 9B, in an embodiment, the movable member 120 may have a shape having a length extending from one end 121 to the other end 122. The third housing 430 may include an opening 1114 and the extension 123 of the movable member 120 may be installed to be movable inward or outward of the third housing 430 through the opening 1114. The other end 122 of the movable member 120 may be disposed inside the third housing 430 and the extension 123 connecting the one end 121 and the other end 122 of the movable member 120 may be disposed to pass through the opening 1114 of the third housing 430.

Referring to FIGS. 5A, 5B, 8A, 8B, 9A, and 9B, in an embodiment, the one end 121 of the movable member 120 may be coupled to an opening 520 formed in the third surface 4003 of the third housing 110. The one end 121 of the movable member 120 may include an insertion portion 1211 (see FIGS. 9A and 9B) inserted into the opening 520. According to an embodiment, the one end 121 of the movable member 120 and the insertion portion 1211 of the third housing 110 may be designed as a pin-connected construction. The insertion portion 1211 may include one or more pin holes 1212 and 1213. The third housing 430 may have pin holes 522 and 523, which are aligned with one or more pin holes 1212 and 1213 (see FIGS. 9A and 9B) when the insertion portion 1211 of the movable member 120 is fitted into the opening 520 of the third housing 110. When the insertion portion 1211 of the movable member 120 is fitted into the opening 520 of the third housing 110 and the pins 531 and 532 are coupled to the pin holes 1212 and 1213 of the movable member 120 and the pin holes 522 and 523 of the third housing 430, the one end 121 of the movable member 120 may be fixed to the third housing 430. According to various embodiments, although not illustrated, the one end 121 of the movable member 120 may be coupled to the third housing 430 using various coupling means (e.g., adhesive and bolting).

Referring to FIGS. 5A and 5B, the extension 123 of the movable member 120 may include a first extension 541 capable of protruding to the outside of the third housing 110, and a second extension 542 connecting the first extension 541 and the other end 122. Since the opening 1114 of the third housing 430 is disposed at a position, which is spaced apart from the position where the one end 121 of the movable member 120 is fixed, along the outer circumference of the third surface 4003, the first extension 541 may be in a convex shape (e.g., an arc-shaped or curved shape) (e.g., the protrusion 124 of FIG. 4) protruding to the outside of the housing 110. The extension 123 of the movable member 120 may be pushed into the third housing 430 or pulled out of the third housing 430 through the opening 1114 of the third housing 430, and a portion (e.g., the protrusion 124 of FIG. 4) of the first extension 541, which protrudes to the outside of the third surface 4003, may be resized.

According to various embodiments, the first extension 541 of the movable member 120 may be designed to include a flexible material. When the ear wearable device 1 is worn in the ear, the portion (e.g., the protrusion 124 of FIG. 4) of the first extension 541, which protrudes to the outside of the third surface 4003, may elastically support the inner surface of the helix, whereby the fit between the housing 110 and the ear can be improved.

Referring to FIGS. 4, 8B, 9A, and 9B, the ear wearable device 1 may include a button 140 coupled to the hole 1111 formed in the third surface 4300 of the third housing 430. According to an embodiment, when an external force is applied to the exposed portion 1401 of the button 140, the button 140 may be guided by the hole 1111 so as to be translationally moved inward of the third housing 430, and may be placed in the pushed state.

Referring to FIGS. 9A and 9B, in an embodiment, the third housing 430 may include a fourth inner space 94 connected to the hole 1111. Referring to FIGS. 8A and 8B again, in an embodiment, a fourth inner space 94 is a groove recessed in a direction directed from surface 4010 of the third housing 430 to the eleventh surface 4011 (see FIG. 5) (the sixth direction 16 in FIG. 1).

Referring to FIGS. 8B, 9A and 9B, in an embodiment, the button 140 may include a 4-1 part 141 slidably coupled to the hole 1111 of the third housing 430, a 4-2 part 142 or a part 4-3 part 143 extending from the one surface 144 of the 4-1 part 141 to protrude in the pushing direction 900 of the button 140. The 4-2 part 142 or the 4-3 part 143 may be disposed in the fourth inner space 94.

The ear wearable device 1 may include an elastic member disposed in the fourth inner space 94 of the third housing 430. The elastic member is able to elastically support the button 140 so as to return the button 140 to the un-pushed state when the external force applied to the button 140 is released. According to an embodiment, the elastic member may be a coil spring 950 disposed to pass through the 4-2 part 142 or the 4-3 part 143. Although one coil spring 950 disposed through the 4-3 part 143 is illustrated, a coil spring disposed through the 4-2 part 142 may be further added.

According to an embodiment, the 4-2 part 142 or the 4-3 part 143 may have a cylindrical shape. One end 951 of the coil spring 950 may be supported by the surface 144 of the 4-1 part 141 to which the 4-2 part 142 and the 4-3 part 143 are connected. The other end 952 of the coil spring 950 may be supported by the surface 941 of the fourth inner space 94, which faces the surface 144.

The button 140 may be designed not to be released to the outside of the third housing 430. Referring to FIG. 8B, in an embodiment, the third housing 430 may include a hole 820 formed in surface 4010, and the button 140 may include a protrusion (e.g., the pin 810) protrudes from the 4-1 part 141 and is disposed in the hole 820. The hole 820 may have an elongated shape having a width 821 and extending in the direction of movement of the button 140. The button 140 may be prevented from being released from the third housing 430 due to the pin 810 and the hole 820. Referring to FIGS. 8B and 9A, in another embodiment, the 4-1 part 141 of the button 140 may be designed to include a portion 145 that covers a portion of one surface 942 of the fourth inner space 94, which may prevent the button 140 from being released from the third housing 430.

Referring to FIGS. 9A and 9B, in an embodiment, the third housing 430 may include a fifth internal space 95 connected to the opening 1114. The movable member 120 may be guided to the fifth inner space 95 and may be moved inward or outward of the third housing 430 through the opening 1114. According to an embodiment, the fifth inner space (or a passage) 95 may be in the form of being disposed along a portion of the outer circumference of the third surface 4003.

According to an embodiment, the fifth inner space 95 may be connected to the fourth inner space 94. The end 122 of the movable member 120 may be disposed in the fourth inner space 94 and the extension 123 of the movable member 120 may be disposed in the fifth inner space 95.

The end 122 of the movable member 120 may be designed not to be released to the outside of the third housing 430. According to an embodiment, the end 122 of the movable member 120 may be designed such that it cannot pass through a gap 93 between the fifth inner space 95 and the fourth inner space 94. Referring to FIGS. 5A, 5B, 9A, and 9B, the end 122 of the movable member 120 may be designed in a shape 941 having a larger cross-sectional area than the extension 123 of the movable member 120.

The ear wearable device 1 may include a locking/unlocking device that enables movement of the extension 123 of the movable member 120 when the button 140 is in the pushed state and hinders movement of the extension 123 of the movable member 120 when the button 140 is in the un-pushed state. Referring to FIGS. 9A and 9B, in an embodiment, the second extension 542 of the movable member 120 may include a twelfth surface 4012 directed to the inside of the third housing 430, and a thirteenth surface 4013 directed to the outside of the third housing 430. According to an embodiment, the locking/unlocking device may include a penetration portion 1402 formed in the button 140. The extension 123 of the movable member 120 may be disposed to pass through the penetration portion 1402 of the button 140. The penetration portion 1402 of the button 140 may include a fourteenth surface 4014 facing the twelfth surface 4012 of the movable member 120 and a fifteenth surface 4015 facing the thirteenth surface 4013 of the movable member 120.

Referring to FIG. 9A, in an embodiment, when the button 140 is in the un-pushed state, the fourteenth surface 4014 of the button 140 is brought into contact with the twelfth surface 4012 of the movable member 120, and the fifteenth surface 4015 of the button 140 may be spaced apart from the thirteenth surface 4013 of the movable member 120. The frictional force between the fourteenth surface 4014 of the button 140 and the thirteenth surface 4012 of the movable member 120 when the button 140 is in the un-pushed state may hinder the extending portion 123 of the movable member 120 from moving inward or outward of the third housing 430.

According to an embodiment, the locking/unlocking device may be designed such that the fourteenth surface 4014 of the button 140 and the twelfth surface 4012 of the movable member 120 is increased when the button 140 is in the un-pushed state. According to an embodiment, the fourteenth surface 4014 of the button 140 and the twelfth surface 4012 of the movable member 120 may be designed to have a mechanical engagement (meshing) structure. Referring to FIGS. 5A and 5B again, the locking/unlocking device may include a concave-convex surface (e.g., a serrated surface 543) formed on the twelfth surface 4012 of the movable member 120. The locking/unlocking device may include a serrated surface formed on the fourteenth surface 4014 of the button 140. When the button 140 is in the un-pushed state, the serrated fourteenth surface 4014 of the button 140 can be engaged with the serrated twelfth surface 4012 of the movable member 120. For example, the fourteenth surface 4014 and the twelfth surface 4012 can be engaged with each other like gears. The engagement between the fourteenth surface 4014 of the button 140 and the twelfth surface 4012 of the movable member 120 is able to increase the coupling force between the button 140 and the extension 123 of the movable member 120, and is able to make it more difficult for the extension 123 of the movable member 120 to move inward or outward of the third housing 430.

Referring to FIG. 9B, in an embodiment, when the button 140 is moved in the pushing direction 900 (e.g., the pushed state), the fourteenth surface 4014 of the button 140 may be separated from the twelfth surface 4012 of the movable member 120. When the button 140 is in the pushed state, the coupling force between the fourteenth surface 4014 of the button 1400 and the twelfth surface 4012 of the movable member 120 is reduced, so that the second housing 123 of the movable member 120 is in the state of being movable inward or outward of the third housing 430. The movable member 120 may include a flexible material (e.g., rubber or silicon). When the extension 123 of the movable member 120 is moved into the third housing 430, a portion of the extension 123 of the movable member 120 is arranged in a curved shape along the inner surface of the third housing 430.

According to an embodiment, when the button 140 is in the pushed state, the fifteenth surface 4015 of the button 140 may be brought into contact with the thirteenth surface 4013 of the movable member 120. Even if the button 140 is in the pushed state, when the extension 123 of the movable member 120 is moved inward or outward of the third housing 430, the friction force between the fifth surface 4015 of the button 140 the third surface 4013 of the movable member 120 may exist.

According to various embodiments, a design may be made such that, when the extension 123 of the movable member 120 is moved in the state in which the button 140 in the pushed state, the frictional force between the 15th surface 4015 of the button 140 and the third surface 4013 of the movable member 120 is reduced. According to an embodiment, when the button 140 is in the pushed state, the fifteenth surface 4015 of the button 140 may be designed so as not to come into contact with the third surface 4013 of the movable member 120. Referring to FIG. 8B, the third housing 430 may include a hole 820 formed in surface 4010, and the button 140 may include a pin 810, which protrudes from the 4-1 part 141 and is inserted into the hole 820. The hole 820 may have a width 821 extending in the direction of movement of the pushing member 140. Referring to FIG. 9B, the button 140 is movable only by a predetermined distance in the pushing direction 900 due to the pin 810 and the hole 820. When the button 140 is moved by a predetermined distance to be in the pushed state, the fifteenth surface 4015 of the button 140 may be separated from the third surface 4013 of the movable member 120. According to various embodiments, although not illustrated, a design may be made such that the 4-2 part 142 or the 4-3 part 143 of the button 140 is moved in the pushing direction 900 so that the surface of the fourth inner space 94 941, and the button 140 is movable only by a predetermined distance in the pushing direction 900.

According to various embodiments, although not illustrated, a design may be made such that in the state in which the button 140 is in the pushed state, the fifteenth surface 4015 of the button 140 and the thirteenth surface 4013 of the movable member 120 are brought into contact with each other. According to an embodiment, the fifteenth surface 4015 of the pushing member 140 or the thirteenth surface 4013 of the movable member 120 may be designed to include a lubricant material such that the frictional force between the two surfaces 4015 and 4013 can be reduced. According to an embodiment, the fifteenth surface 4015 or the thirteenth surface 4013 of the button 140 may be designed to have a concavo-convex shape, so that the friction area between the two surfaces 4015 and 4013 can be reduced.

According to various embodiments, the locking/unlocking device may be designed with various different elements such that, in the state in which the button 140 is in the pushed state, movement (e.g., push-in or pull-out) of the extension 123 of the movable member 120 is enabled and, in the state in which the button 140 is in the un-pushed state, movement of the extension 123 of the movable member 120 may be hindered.

Figure 10:
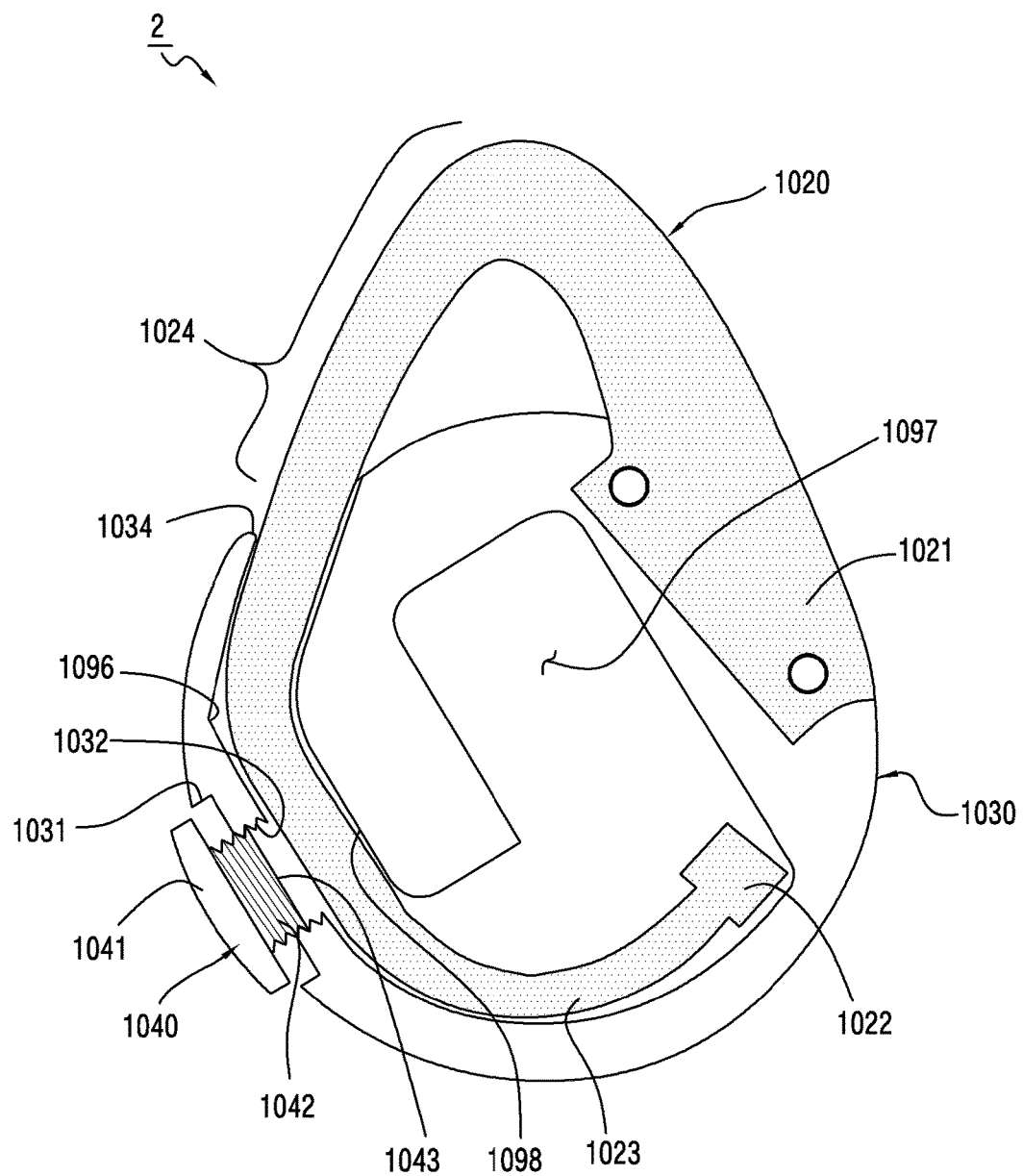
FIG. 10 is a cross-sectional view of a movable member, which is movable inward or outward of the housing of the ear wearable device in various embodiments, in the state of being coupled to the housing.

FIG. 10 is a cross-sectional view of a movable member, which is movable inward or outward of the housing of the ear wearable device in various embodiments, in the state of being coupled to the housing.

Referring to FIG. 10, an ear wearable device 2 may include a housing 1030 and a movable member 1020 coupled to the housing 1030 to be movable inward or outward of the housing 1030. According to various embodiments, the housing 1030 may be in the form of including a generally annular third surface 4003 like the third housing 430 of FIGS. 5A and 5B. According to various embodiments, although not illustrated, the ear wearable device 2 may further include another housing (e.g., the first housing 410 or the second housing 420 of FIG. 5A) coupled to the housing 1030. According to various embodiments, the ear wearable device 2 may be designed to include at least some of the elements of FIG. 3.

The housing 1030 may include an opening 1034, and the movable member 1020 may be installed to be movable inward or outward of the housing 1030 through the opening 1034. The extension 1023, which connects the one end 1021 and the other end 1022 of the movable member 1020, may be disposed to pass through the opening 1034 of the housing 1030, and the other end 1022 of the movable member 1020 may be disposed in the housing 1030. The one end 1021 of the movable member 1020 may be fixed to the housing 1030 at a position spaced away from the opening 1034, so that the movable member 1020 coupled to the housing 1030 may provide a protrusion 1024 in the form of protruding outward of the housing 1030. According to an embodiment, the extension 1023 of the movable member 1020 may be pushed into the housing 1030 or pulled out of the housing 1030 through the opening 1034 of the housing 1030, so that the protrusion 1024 can be resized.

According to an embodiment, the housing 1030 may include a inner space 1096 that is connected to the opening 1034. The movable member 1020 may be guided to the inner space 1096 and may be moved inward or outward of the housing 1030 through the opening 1034. According to an embodiment, the housing 1030 may include a inner space 1097 that is connected to the inner space 1096. The end 1022 of the movable member 1020 may be disposed in the inner space 1097.

According to various embodiments, the movable member 1020 may be in a form that does not include a serrated surface 543 in the movable member 1020 of FIGS. 5A and 5B.

According to an embodiment, the housing 1030 may include a hole 1031 having bolting threads 1032. The hole 1031 may be connected to the space (e.g., the sixth inner space 1096) in which the extension 1023 of the movable member 1020 is disposed. According to an embodiment, the ear wearable device 2 may include a bolt 1040 that can be fastened to the hole 1031 in the housing 1030. The bolt 1040 may include a threaded cylindrical rod (or shaft) 1042 and a head 1041 connected to the rod 1042.

According to an embodiment, when the bolt 1040 is fastened to the hole 1031 and moved forward, the end 1043 of the bolt 1040 is able press the extension 1023 of the movable member 1020. Since the extension 1023 of the movable member 1020 is disposed in the space having a width smaller than the thickness of the extension 1023 (e.g., the width between the end 1043 of the bolt 1040 and the inner wall 1098 of the housing 1030), the extension is not freely moved. According to various embodiments, the ear wearable device 2 may be designed such that the frictional force between the end 1043 of the bolt 1040 and the extension 1023 of the movable member 1020 is increased. According to an embodiment, the end 1043 of the bolt 1040 may include a pointed shape.

When the bolt 1040 is moved back, the end 1043 of the bolt 1040 does not press the extension 1023 of the movable member 1020, and the extension 1023 of the movable member 1020 be in the state in which the extension 1023 is movable inward or outward of the housing 1030.

According to various embodiments, the hole 1031 in the housing 1030 may include a space 1031 in which the head 1041 of the bolt 1040 is accommodated. When the bolt 1040 is fastened to the hole and is moved forward, the head 1041 of the bolt 1040 may be disposed in the space 1031 of the hole 1031. The exposed surface of the head 1041 accommodated in the space 1031 may be smoothly connected to the outer surface of the housing 1030 and may form a portion of the external appearance of the ear wearable device 2.

According to various embodiments, the head 1041 of the bolt 1040 may include a groove (not illustrated). When a screwdriver, a nail, or the like is fitted into the groove and is rotated, the bolt 1040 can be rotated to be moved forward or backward in the hole 1031.

Figure 11A:
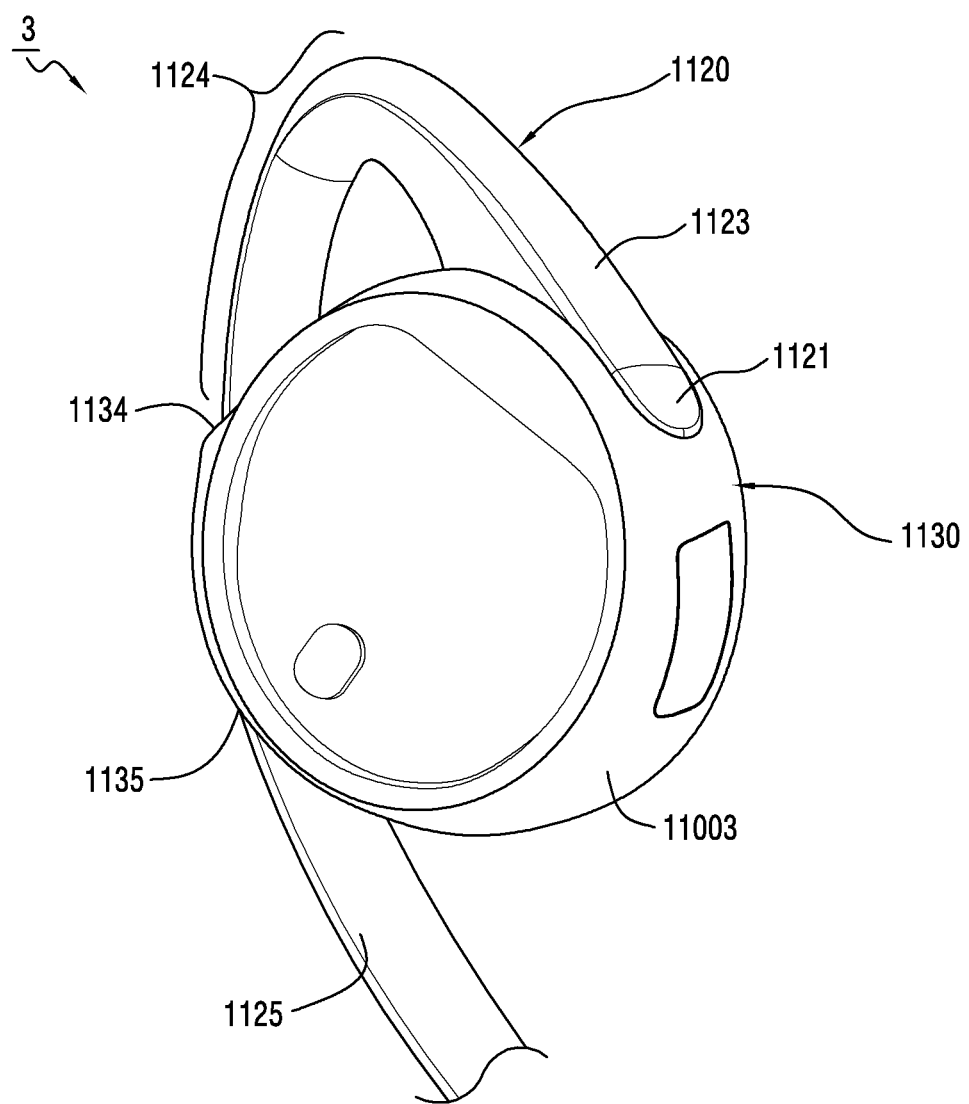
FIG. 11A illustrates a state in which the movable member is coupled to the housing of the ear wearable device in various embodiments.
Figure 11B:
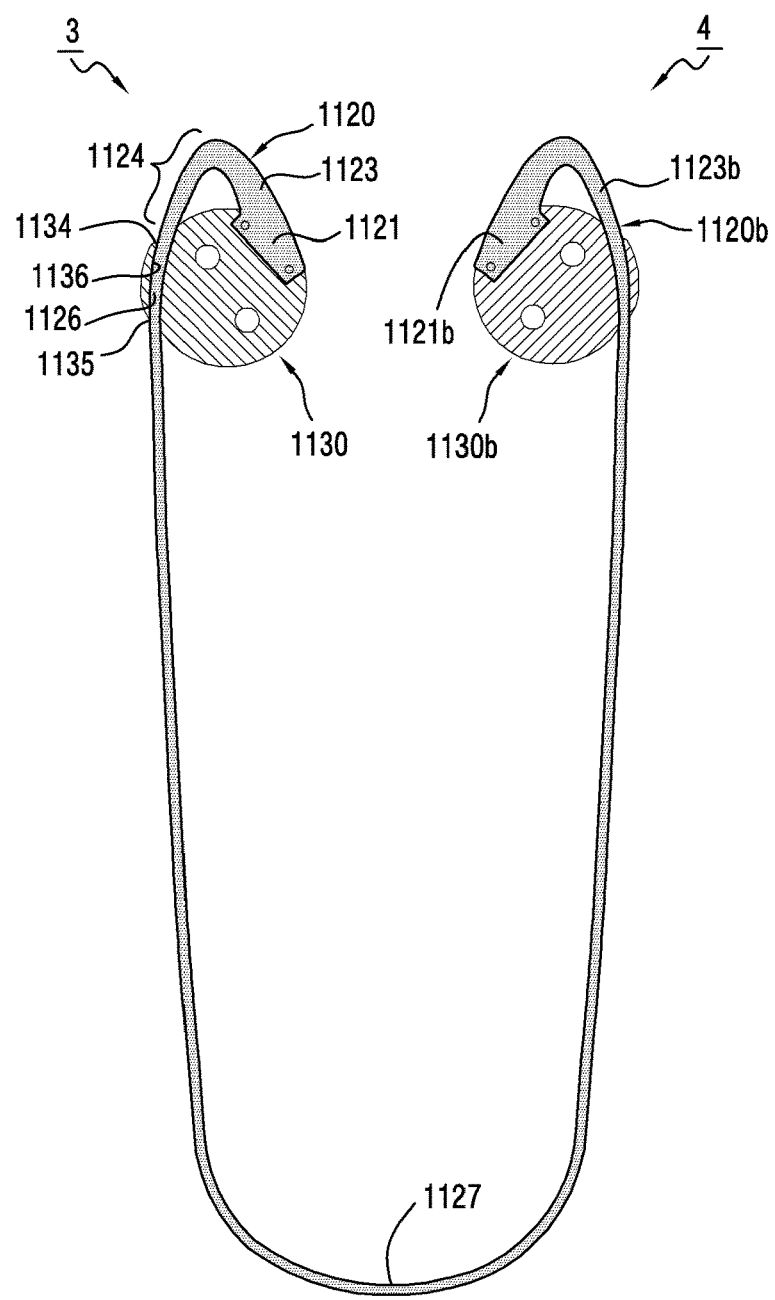
FIG. 11B is a cross-sectional view illustrating a state in which the movable member is coupled to the housing of the ear wearable device in various embodiments.
Figure 11C:
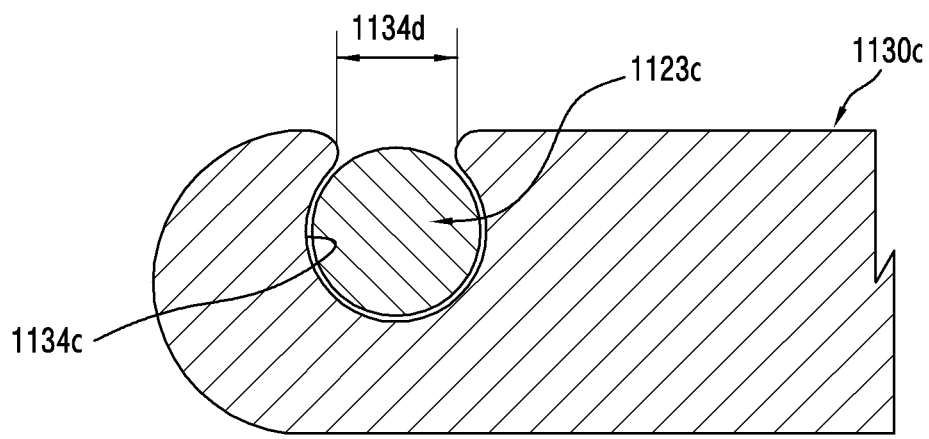
FIG. 11C is a cross-sectional view illustrating a coupled state between the movable member and the housing according to another embodiment.

FIG. 11A illustrates a state in which the movable member is coupled to the housing of the ear wearable device in various embodiments. FIG. 11B is a cross-sectional view illustrating a state in which the movable member is coupled to the housing of the ear wearable device in various embodiments. FIG. 11C is a cross-sectional view illustrating a coupled state between the movable member and the housing according to another embodiment.

Referring to FIGS. 11A and 11*b*, an ear wearable device 3 may include a housing 1130 and a movable member 1120 coupled to the housing 1130 to be movable in the housing 1130. According to an embodiment, the housing 1130 may be in the form of including a generally annular outer circumferential surface (or circumferential edge) 11003 (e.g., the third surface 4003 of FIGS. 5A and 5B). According to various embodiments, although not illustrated, the ear wearable device 3 may further include another housing (e.g., the first housing 410 or the second housing 420 of FIG. 5A) coupled to the housing 1130. The housing 1130 may include a fourth opening 1134 and a fifth opening 1135 disposed at different positions along the outer circumferential surface 11003. The housing 1130 may include a passage (or an inner space) 1136 connecting the fourth opening 1134 and the fifth opening 1135. The movable member 1120 may include an extension 1123 extending from the one end 1121 thereof, and the extension 1123 may be disposed to pass through the passage 1136 of the housing 1130.

According to an embodiment, the one end 1121 of the movable member 1120 may be fixed to the housing 1130 at a position spaced away from the fourth opening 1134, so that the movable member 1120 coupled to the housing 1130 may provide an A-portion 1124 in the form of protruding outward of the fourth opening 1134 (or a protrusion 1124). According to an embodiment, one end 1121 of the movable member 1120 may be coupled to an opening 520 (e.g., see FIG. 8A) formed in the housing 1130, as in FIG. 8A. The A-portion 1124 of the movable member 120 may be used for coupling the ear wearable device to the groove of the auricle (e.g., a space connected to the ear canal) together with at least a portion of the housing 1130. The extension 1123 of the movable member 1120 may include a B-portion 1126 disposed in the passage 1136 and a C-portion 1125 located outside the fifth opening 1135. According to an embodiment, when an external force is applied that overcomes the frictional force between the passage 1136 and the B-portion 1126 acts, the extension 1123 of the movable member 1120 slides over the passage 1136, and the size of the A-portion 1124 (or the C-portion 1125) may be adjusted.

According to an embodiment, the movable member 1120 may include a flexible material (e.g., rubber or silicon). When the ear wearable device 3 is coupled to the groove of the auricle, the A-portion 1124 of the movable member 1120 may be resized such that the A-portion 1124 of the movable member 1120 resiliently supports the inner surface of the helix of the ear. A design may be made such that when the A-portion 1124 of the movable member 1120 elastically supports the inner surface of the helix of the ear, the frictional force between the passage 1136 and the B-portion 1126 hinders the extension 1123 of the movable member 1120 from sliding in the passage 1136.

The frictional force between the B-portion 1126 of the movable member 1120 and the passage 1136 of the housing 1130 may be variously designed depending on the material forming the extension 1123 of the movable member 1120 or the passage 1136 of the housing 1130, or the shape thereof. According to an embodiment, the B-portion 1126 of the movable member 1120 may be designed to have a thickness larger than the width of the passage 1136 and to be resiliently fitted into the passage 1136. According to various embodiments, the outer surface of the B-portion 1126 of movable member 1120 or the inner surface of passage 1136 may be designed as a rough surface. According to various embodiments, the outer surface of the B-portion 1126 of the movable member 1120 may be formed of a material which is the same as or different from that of the inner surface of the passage 1136.

Referring to FIG. 11C, in another embodiment, the housing 1130*c* may include a recessed groove 1134*c* and an extension 1123*c* of the movable member (e.g., the extension 1120 of FIG. 11A) may be configured to having a detachable structure with respect to the groove 1134*c*. In an embodiment, the extension 1123*c* of the flexible movable member may be designed to be resiliently fitted into the groove 1134*c* formed in the housing 1130*c*. According to various embodiments, the width 1134*d* of the inlet and outlet of the groove 1134*c* may be designed to be smaller than the thickness of the extension 1123*c* of the flexible movable member. According to various embodiments, the cross-sectional shape of the groove 1134*c* may be variously designed in a circular shape, a polygonal shape, or the like.

The ear wearable device 3 may be a device that is wearable on a right ear. Referring to FIG. 11B, an ear wearable device 4, which is wearable on the left ear, may include a housing 1130*b* and a movable member 1120*b* coupled to the housing 1130*b* to be movable in the housing 1130*b*, and may be designed to be symmetrical to the ear wearable device 3, which is wearable on the left ear. According to various embodiments, the ear wearable device 3 or 4 may be designed to include at least some of the elements of FIG. 3.

According to an embodiment, the movable member 1220 of one ear wearable device 4 and the movable member 1120 of the other ear wearable device 3 may be integrally formed. The movable member 1120*b* of the one ear wearable device 4 may include an end portion 1121*b* fixed to the housing 1130*b* and an extension 1123*b* extending from the end portion 1121*b*. The extension 1123*b* may be connected to the extension 1123 of the other wearable device 3.

According to an embodiment, since the two ear wearable devices 3 and 4 are connected by a connecting wire 1127 (e.g., the extensions 1123 and 1123*b*), the user may more easily carry both of the ear wearable devices 3 and 4 in comparison with an embodiment in which the two ear wearable devices are separated from each other. According to an embodiment, when the two ear wearable devices 3 and 4 are worn on both ears of a user, the connecting line 1127 between the two ear wearable devices 3 and 4 may be designed to be hung down so as to be disposed on the rear side of the user's neck.

According to various embodiments, the connecting line 1127 may be designed to electrically connect the two ear wearable devices 3 and 4. One end 1121 (e.g., see FIG. 11B) of the connecting line 1127 may be electrically connected to a circuit mounted on one ear wearable device 3. The other end 1121b (e.g., see FIG. 11B) of the connecting line 1127 may be electrically connected to a circuit mounted on the other ear wearable device 4.

According to various embodiments, the connecting line 1127 may be designed as a path that moves audio data from a first ear wearable device to a second ear wearable device. According to an embodiment, the first ear wearable device may reproduce audio data (e.g., nonvolatile audio data or volatile audio data) stored in a memory 350 (see FIG. 3), may output the reproduced audio data through the speaker 341 (see FIG. 3), and may transmit the reproduced audio data (e.g., an audio signal) to the second ear wearable device via the connecting line 1127. The audio signal from the first ear wearable device may be output through the speaker of the second ear wearable device. According to another embodiment, the first ear wearable device may reproduce audio data (e.g., nonvolatile audio data or volatile audio data) stored in a memory 350 (see FIG. 3), may output the reproduced audio data through the speaker 341 (see FIG. 3), and may transmit the audio data (e.g., an audio signal) to the second ear wearable device via the connecting line 1127. The second wearable device may reproduce the audio data received from the first ear wearable device and may output the audio data through the speaker. According to another embodiment, the first ear wearable device may receive an audio signal (e.g., audio data reproduced by an external device) from an external device (e.g., a smart phone), may output the audio signal through a speaker 341, and may transmit the received audio data to the second ear wearable device via the connecting line 1127. The audio signal from the first ear wearable device may be output through the speaker of the second ear wearable device.

According to various embodiments, the connecting line 1127 may be designed as a path that moves power from a first ear wearable device to a second ear wearable device. According to an embodiment, the first ear wearable device may include a battery, but the second ear wearable device may not include a battery. The first ear wearable device may transmit power to the second ear wearable device via the connecting line 1127. According to another embodiment, each of the two ear wearable devices may include a battery. When the residual amounts of the batteries of the two ear wearable devices are in an unbalanced state, power exchange between the two ear wearable devices may be performed via the connecting line 1127. This allows the residual amounts of the batteries of both ear wearable devices to be in balance.

In addition, various signals may be exchanged between the two ear wearable devices via the connecting line 1127.

According to an embodiment of the present disclosure, an ear wearable device 1 (see FIG. 1) may include: a housing 110 (see FIG. 1) including a portion configured to be inserted into the helix of the ear; a speaker 341 (see FIG. 3) disposed inside the housing 110 to be directed to an eardrum when the housing 110 is inserted into the concha of the ear; a button 140 (see FIG. 1) coupled to a hole 1111 (see FIG. 1) formed in the housing 110 and partially exposed to the outside, and moved into the housing 110 to be placed in a pushed state when an external force is applied to the exposed portion; an elastic member (the coil spring 950 in FIG. 8B) disposed in the housing 110 and configured to elastically support the button 140 so as to return the button 140 to an un-pushed state when the external force is released; and a movable member 120 (see FIG. 1) including a portion protruding through an opening 1114 formed in the housing 110, and installed to be pushed into the opening 1114 or pulled out of the opening 1114 such that the protruding portion 124 can be extended or retracted when the button is in a pushed state.

According to an embodiment of the present disclosure, the protruding portion 124 of the movable member 120 may be used to couple the ear wearable device to the helix of the ear together with at least a portion of the housing 110 when the housing 110 is inserted into the concha of the ear.

According to an embodiment of the present disclosure, the movable member 120 may be a flexible member having a length extending from a first end 121 to a second end 122 thereof. The first end 121 may be connected to the housing 110. The second end 122 may be disposed within the housing 110. An extension 123 connecting the first end 121 and the second end 122 may be disposed to pass through the opening 1114. The extension 123 of the movable member 120 may be movable inward or outward of the housing 110 through the opening 1114.

According to an embodiment of the present disclosure, the button 140 may include a penetration portion 1402 through which the extension 123 of the movable member 120 passes. When the button 140 is in the un-pushed state, one surface (the fourteenth surface 4014 in FIG. 9A) of the penetration portion 1402 is brought into contact with the extension 123 of the movable member 120 so as to hinder push-in or pull-out of the movable member 120. When the button 140 is in the pushed state, one surface 4014 of the penetration portion 1402 is spaced apart from the extension 123 of the movable member 120 so as to enable push-in or pull-out of the movable member.

According to an embodiment of the present disclosure, the ear wearable device may further include a serrated first surface formed on one surface 4014 of the penetration portion 1402 and a serrated second surface 543 (see FIG. 9A) formed on the extension 123 of the movable member 120. When the button 140 is in the un-pushed state, the first surface and the second surface may be engaged with each other.

According to an embodiment of the present disclosure, the housing 110 may include a first space (a fifth inner space 95 in FIG. 9A), which is connected to the opening 1114 and in which an extension 123 of the movable member 120 is disposed, and a second space (the fourth inner space 94 in FIG. 9A) in which the second end 122 of the movable member 120 is disposed. The second end 122 may have a shape having a larger cross-sectional area than the extension 123 of the movable member 120 so as to prevent the second end 122 from moving into the first space 95.

According to an embodiment of the present disclosure, the housing 110 may include a first surface 4001 (see FIG. 4) including a second opening 1121 (see FIGS. 2A, 2B, 2C, 2D, 2E and 2F) configured to discharge sound output from the speaker 41 (see FIG. 3) to the outside, a second surface 4002 (see FIG. 4) disposed at an opposite side to the first surface, and an annular third surface 4003 (see FIG. 4)

connecting the first surface 4001 and the second surface 4002. The opening 1114, through which the extension 123 of the movable member 120 passes, is disposed on the third surface 4003, and one end 121 of the movable member 120 may be connected to the third surface 4003.

According to an embodiment of the present disclosure, the hole 1114 (see FIG. 4) for the push member 140 may be disposed on the third surface 4003.

According to an embodiment of the present disclosure, the first end 121 may be inserted into a third opening 520 (see FIG. 9A) disposed on the third surface 4003, and may be fixed to the housing 110.

According to an embodiment of the present disclosure, the first end 121 may be fixed to the housing 110 through a pin connection.

According to an embodiment of the present disclosure, the housing 110 may include a space (the fifth inner space 95 in FIG. 9A) which is connected to the opening 1114 through which the extension 123 of the movable member 120 passes is and in which the extension 123 of the movable member 120 is disposed. The space 95 may have a shape disposed along the outer circumference of the third surface 4003.

According to an embodiment of the present disclosure, the housing 110 may include a first housing 410 (see FIGS. 5A and 5B) forming the first surface 4001, a second housing 420 (see FIGS. 5A and 5B) forming the second surface 4002, and a third housing 430 (see FIGS. 5A and 5B) forming the third surface 4003.

According to an embodiment of the present disclosure, the button 140, the movable member 120, and the elastic member 950 may be installed in the third housing 430.

According to an embodiment of the present disclosure, the speaker 341 may be disposed in the first housing 410 (in the first inner space 63 in FIG. 6).

According to an embodiment of the present disclosure, the ear wearable device 1 may further include a touch pad disposed in the housing (in the second inner space 73 in FIG. 7) along at least a portion of the second surface 4002.

According to an embodiment of the present disclosure, the ear wearable device 1 may further include an optical sensor disposed in the housing 110 to be aligned with a light transmissive region 150 (see FIGS. 2A, 2B, 2C, 2D, 2E and 2F) formed on the third surface 4003.

According to an embodiment of the present disclosure, the optical sensor may be a heart rate sensor.

According to an embodiment of the present disclosure, the button 140 may include a first portion (the first part 141 in FIG. 9A) slidably installed in the hole 1111, and at least one second portion (the second part 142 in FIG. 9A) or a third portion (the third part 143 in FIG. 9A) protruding in the moving direction 900 of the button 140 from the first portion 141. The elastic member may be a coil spring 950 penetrating the second portion 142 or 143.

According to an embodiment of the present disclosure, the housing (the third housing 430 in FIG. 8B) may include a second hole 820, which is narrow and long in the moving direction of the button 140. The button 140 may include a protrusion 810 protruding in a direction perpendicular to the moving direction and disposed in the second hole 820.

According to an embodiment of the present disclosure, the ear wearable device 1 may include a battery 370 (see FIG. 3) disposed in the housing 110, a memory 350 (see FIG. 3) disposed in the housing 110 to store audio data, and a processor 380 (see FIG. 3) disposed in the housing 110 and electrically connected to the speaker 341, the battery 370, and the memory 350. The memory 350 may include an instruction, which causes the processor 380 to output audio data stored in the memory 350 via the speaker 341 when executed.

According to an embodiment of the present disclosure, the ear wearable device 1 may further include a wireless communication circuit 310 (see FIG. 3) disposed in the housing 110 and electrically connected to the processor 380. The memory 350 may include an instruction to cause the processor 380 to receive the audio data from an external device using the wireless communication circuitry 380 when executed.

The present disclosure has been described above in connection with the exemplary embodiments thereof. It will be understood by those skilled in the art to which the present disclosure belongs that the present disclosure may be implemented in modified forms without departing from the essential characteristics of the present disclosure. Therefore, the embodiments disclosed herein should be considered from an illustrative point of view, rather than a limitative point of view. The scope of the present disclosure is found not in the above description but in the accompanying claims, and all differences falling within the scope equivalent to the claims should be construed as being included in the present disclosure.

What is claimed is:

1. An ear wearable device comprising:
   a housing comprising a portion shaped to be inserted into a concha of the ear;
   a speaker disposed inside the housing and configured to be disposed in an auditory canal when the housing is inserted into the concha of the ear;
   a button emerging from a hole formed in the housing;
   an elastic member disposed in the housing and elastically resisting an external force against the button; and
   a movable member including a portion protruding through an opening formed in the housing, and configured to be pushed into the opening or pulled away from the opening such that a protruding portion can be pushed or pulled when the button is pressed,
   wherein the button includes a penetration portion through which an extension of the movable member passes.

2. The ear wearable device of claim 1, wherein the protruding portion of the movable member configured to touch a helix of the ear when the housing is inserted into the concha of the ear.

3. The ear wearable device of claim 1, wherein the movable member is a flexible member having a length extending from a first end to a second end thereof,
   the first end is connected to the housing, the second end is disposed within the housing, and an extension connecting the first end and the second end is disposed to pass through the opening, and
   the extension of the movable member is movable inward or outward of the housing through the opening.

4. The ear wearable device of claim 3,
   when the button is un-pushed, one surface of the penetration portion is brought into contact with the extension of the movable member so as to hinder push-in or pull-out of the movable member, and
   when the button is pushed, one surface of the penetration portion is spaced apart from the extension of the movable member so as to enable push-in or pull-out of the movable member.

5. The ear wearable device of claim 4, further comprising:
   a serrated first surface formed on one surface of the penetration portion and a serrated second surface formed on the extension of the movable member, wherein, when the button is not pushed, the serrated first surface and the serrated second surface are engaged with each other.

6. The ear wearable device of claim 3, wherein the housing includes a first space, which is connected to the opening and in which the extension of the movable member is disposed, and a second space in which the second end of the movable member is disposed, and the second end has a shape having a larger cross-sectional area than the extension of the movable member so as to prevent the second end from moving into the first space.

7. The ear wearable device of claim 3, wherein the housing includes a first surface including a second opening configured to discharge sound output from the speaker to the outside, a second surface disposed at an opposite side to the first surface, and an annular third surface connecting the first surface and the second surface, the opening, through which the extension of the movable member passes, is disposed on the annular third surface, and one end of the movable member is connected to the annular third surface.

8. The ear wearable device of claim 7, wherein the hole for the button is disposed on the annular third surface.

9. The ear wearable device of claim 7, wherein the first end is inserted into a third opening disposed on the annular third surface, and is fixed to the housing.

10. The ear wearable device of claim 7, wherein the housing includes a space, which is connected to the opening through which the extension of the movable member passes, and in which the extension of the movable member is disposed, and the space has a shape disposed along an outer circumference of the annular third surface.

11. The ear wearable device of claim 7, wherein the housing includes a first housing forming the first surface, a second housing forming the second surface, and a third housing forming the annular third surface.

12. The ear wearable device of claim 11, wherein the button, the movable member, and the elastic member are installed in the third housing.

13. The ear wearable device of claim 11, wherein the speaker is disposed in the first housing.

14. The ear wearable device of claim 7, further comprising:

a touch pad disposed in the housing along at least a portion of the second surface.

15. The ear wearable device of claim 7, further comprising:

an optical sensor disposed in the housing to be aligned with a light transmissive region formed on the annular third surface.

16. The ear wearable device of claim 15, wherein the optical sensor is a heart rate sensor.

17. The ear wearable device of claim 1, wherein the button includes a first portion slidably installed in the hole, and at least one second portion or a third portion protruding in a moving direction of the button from the first portion, and the elastic member is a coil spring penetrating the second portion.

18. The ear wearable device of claim 17, wherein the housing includes a second hole, which is narrow and long in a moving direction of the button, and the button includes a protrusion protruding in a direction perpendicular to the moving direction and disposed in the second hole.

19. The ear wearable device of claim 1, further comprising:

a battery disposed in the housing;
a memory disposed in the housing to store audio data; and
one or more processors disposed in the housing and electrically connected to the speaker, the battery, and the memory,
wherein the memory includes a plurality of instructions executable by the one or more processors, which causes the one or more processors to output audio data stored in the memory via the speaker when executed.

20. The ear wearable device of claim 19, further comprising:

a wireless communication circuit disposed in the housing and electrically connected to the one or more processor,
wherein the memory includes an instruction to cause the processor to receive the audio data from an external device using the wireless communication circuit when executed.

* * * * *